(12) United States Patent
Kameda

(10) Patent No.: US 7,260,547 B2
(45) Date of Patent: Aug. 21, 2007

(54) SYSTEM FOR AIDING TO MAKE MEDICAL CARE SCHEDULE AND/OR RECORD, PROGRAM STORAGE DEVICE AND COMPUTER DATA SIGNAL EMBODIED IN CARRIER WAVE

(76) Inventor: Toshitada Kameda, No. 929 Higashi-cho, Kamogawa-shi, Chiba-ken (JP)

( * ) Notice: Subject to any disclaimer, the term of this patent is extended or adjusted under 35 U.S.C. 154(b) by 1310 days.

(21) Appl. No.: 09/974,980

(22) Filed: Oct. 12, 2001

(65) Prior Publication Data
US 2002/0046062 A1 Apr. 18, 2002

(30) Foreign Application Priority Data
Oct. 13, 2000 (JP) ............................. 2000-314394

(51) Int. Cl.
*G06F 17/60* (2006.01)
(52) U.S. Cl. ................... 705/3; 705/7; 705/8; 705/9; 345/440; 345/441; 345/442; 345/443; 346/963
(58) Field of Classification Search .............. 705/2, 705/3, 7–9; 345/440–443, 963
See application file for complete search history.

(56) References Cited

U.S. PATENT DOCUMENTS

| | | | | |
|---|---|---|---|---|
| 4,878,175 | A | * | 10/1989 | Norden-Paul et al. .......... 705/2 |
| 5,065,315 | A | * | 11/1991 | Garcia ............................ 705/2 |
| 5,072,383 | A | * | 12/1991 | Brimm et al. .................. 705/2 |
| 5,247,611 | A | * | 9/1993 | Norden-Paul et al. ....... 715/504 |
| 5,323,314 | A | * | 6/1994 | Baber et al. .................... 705/8 |
| 5,325,478 | A | * | 6/1994 | Shelton et al. ............... 715/507 |

(Continued)

FOREIGN PATENT DOCUMENTS

EP 784283 A1 * 7/1997

(Continued)

OTHER PUBLICATIONS

Kameda; "System for Aiding to Make Medical Care Schedule and/or Record, Program Storage Device and Computer Data Signal Embodied in Carrier Wave"; U.S. Appl. No. 09/639,645, filed Aug. 16, 2000.

(Continued)

*Primary Examiner*—Joseph Thomas
*Assistant Examiner*—Mike Tomaszewski
(74) *Attorney, Agent, or Firm*—Finnegan, Henderson, Farabow, Garrett & Dunner, LLP

(57) ABSTRACT

A system for aiding to make a medical care schedule and/or record is provided with: a plurality of files for respectively including medical care data in correlation with execution timing data; a display controlling device for (i) generating first display data to display the medical care data composing the medical care schedule and/or record for one patient, as for only a partial period for the one patient, and (ii) generating second display data to display a table identification mark information, as a patient chronological table in which the table identification mark information is arranged at a position corresponding to the partial period on a time axis indicating the whole period of the medical care schedule and/or record; and a selecting device for selecting one of a plurality of table identification mark information.

18 Claims, 14 Drawing Sheets

U.S. PATENT DOCUMENTS

| | | | | |
|---|---|---|---|---|
| 5,361,202 | A | * | 11/1994 | Doue .......................... 705/3 |
| 5,447,164 | A | * | 9/1995 | Shaya et al. ................ 600/523 |
| 5,682,526 | A | * | 10/1997 | Smokoff et al. ......... 707/104.1 |
| 5,788,646 | A | * | 8/1998 | Fuchs et al. ................ 600/523 |
| 5,830,150 | A | * | 11/1998 | Palmer et al. .............. 600/523 |
| 5,913,197 | A | * | 6/1999 | Kameda ........................ 705/3 |
| 5,921,920 | A | * | 7/1999 | Marshall et al. ............ 600/300 |
| 5,923,018 | A | * | 7/1999 | Kameda et al. ............. 235/385 |
| 5,936,625 | A | * | 8/1999 | Kahl et al. .................. 715/775 |
| 5,950,168 | A | * | 9/1999 | Simborg et al. ................ 705/3 |
| 5,970,466 | A | * | 10/1999 | Detjen et al. .................. 705/8 |
| 6,321,203 | B1 | * | 11/2001 | Kameda ........................ 705/3 |
| 6,322,502 | B1 | * | 11/2001 | Schoenberg et al. ......... 600/300 |
| 6,345,260 | B1 | * | 2/2002 | Cummings, Jr. et al. ....... 705/8 |
| 6,380,953 | B1 | * | 4/2002 | Mizuno ....................... 715/764 |
| 6,876,972 | B1 | * | 4/2005 | Kameda ........................ 705/3 |
| 6,957,187 | B1 | * | 10/2005 | Kameda ........................ 705/3 |

FOREIGN PATENT DOCUMENTS

| | | |
|---|---|---|
| JP | 4-84945 | 3/1992 |
| JP | 06-176025 | 6/1994 |
| JP | 8-266483 | 10/1996 |
| JP | 09-106336 | 4/1997 |
| JP | 9-147027 | 6/1997 |
| JP | 9-185651 | 7/1997 |
| JP | 3066658 | 8/1999 |
| JP | 2000-048093 | 2/2000 |

OTHER PUBLICATIONS

Kameda; "System for Aiding to Make Medical Care Schedule, and Program Storage Device Readable by the System"; U.S. Appl. No. 09/330,094, filed Jun. 11, 1999.

* cited by examiner

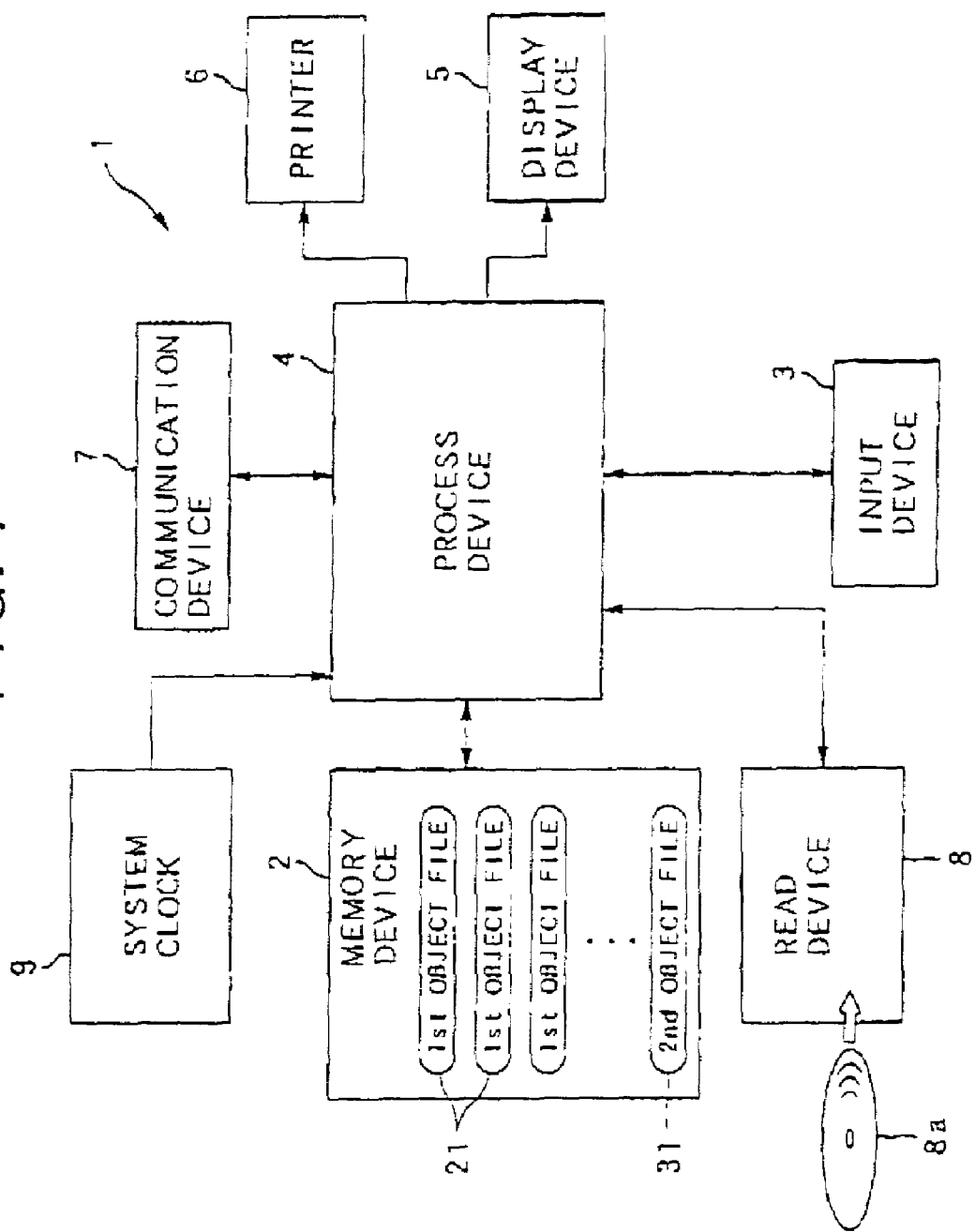

FIG. 2

| RECORD | 12-13-94 (Tues) 1st DAY (CCU) | 12-14-94 (Wed) 2nd DAY (CCU) | 12-15-94 (Thur) 3rd DAY (CCU) | ~ | 12-19-94 (Mon) 7th DAY |
|---|---|---|---|---|---|
| | NURSING SCHEDULE | | | | |
| ACTIVITY RESTRICTION (REST/EXCRETION/CLEANNESS) | BED BATH PUDIC CLEAN WASH HELPER | BED BATH PUDIC CLEAN WASH HELPER | BED BATH | | BED BATH |
| MEAL | | MORNING ○ LUNCH △ DINNER ○ | ○ ○ | | ORDINARY MEAL ○ |
| PRACTICE/MONITOR | VITAL SIGN WEIGHT MEASUREMENT SG CATHETER MONITOR CARDIOGRAM PULSE OXIMETER | VITAL SIGN WEIGHT MEASUREMENT | VITAL SIGN WEIGHT MEASUREMENT | | VITAL SIGN WEIGHT MEASUREMENT ○ |
| TEST | CARDIOGRAM BREAST X RAY CPK, CPK-MB 24 hours FECALURIA | CARDIOGRAM BREAST X RAY CPK, CPK-MB 24 hours FECALURIA | CARDIOGRAM BREAST X RAY CPK, CPK-MB ○ 24 hours FECALURIA | | CARDIOGRAM BREAST X RAY |
| ORAL MEDICINE/ EXTERNAL MEDICINE | | TIMELY ADMINISTRATION ① | TIMELY ADMINISTRATION ① | | TIMELY ADMINISTRATION ① |
| INJECTION | INSTILLATION | INSTILLATION | INSTILLATION ① | | ○ |
| TREATMENT | MT EVULSION S-G EVULSION DIV DELETION WRAPPING NEBLIZER SPIRON | A LINE EVULSION B CASH EVULSION NEBLIZER SPIRON | Y-DRAIN EVULSION NEBLIZER SPIRON | | NEBLIZER SPIRON |

FIG. 8

| EVENT | CONDITION | LAYER NAME |
|---|---|---|
| GENERATION OF HC | THE INTERNAL DEPARTMENT | INTERNAL LAYER |
| | CLINIC | CLINIC LAYER |

FIG. 12

| ... | 12-13-94 | 12-14-94 | 12-15-94 | | 12-19-94 |
|---|---|---|---|---|---|
| ⋮ | ⋮ | ⋮ | ⋮ | | ⋮ |
| TEST | ⋮ | ▭▭ | ▭ | ▭ | ▭▭ |
| MEDI-CATION | ⋮ | ▭▭ | ▭▭ | ▭▭ | ▭▭ |
| INJECTION | ⋮ | | | | |
| MEAL | ⋮ | ▭ | ▭ | ▭ | ▭ |
| REHABILI-TATION | ⋮ | | | | |
| ⋮ | ⋮ | ⋮ | ⋮ | ⋮ | ⋮ |

⬇ THIN OUT EMPTY ROW

| ... | 12-13-94 | 12-14-94 | 12-15-94 | | 12-19-94 |
|---|---|---|---|---|---|
| ⋮ | ⋮ | ⋮ | ⋮ | | ⋮ |
| TEST | ⋮ | ▭▭ | ▭ | ▭ | ▭▭ |
| MEDI-CATION | ⋮ | ▭▭▭ | ▭▭▭ | ▭▭▭ | ▭▭▭ |
| MEAL | ⋮ | ▭ | | ▭ | ▭ |
| ⋮ | ⋮ | ⋮ | ⋮ | ⋮ | ⋮ |

SYSTEM FOR AIDING TO MAKE MEDICAL CARE SCHEDULE AND/OR RECORD, PROGRAM STORAGE DEVICE AND COMPUTER DATA SIGNAL EMBODIED IN CARRIER WAVE

BACKGROUND OF THE INVENTION

1. Field of the Invention

The present invention generally relates to a new system for aiding or navigating a person related to medical care such as a medical doctor, a nurse, a pharmacist, a medical office worker and so on, to make a medical care schedule and a medical care record. The present invention also relates to a compute: readable program storage device and a computer data signal embodiment in a carrier wave, which allow a computer to function as the aiding system.

2. Description of the Related Art

Conventionally, a medical doctor performs an observation or examination for the patient. Then, at first the medical doctor makes up a medical care schedule in his or her mind as for a test, a medical service, an arrangement for hospitalization, a medical operation, an administration of medicine etc., after that in accordance with the observation and the diagnosis Then, for example, the medical doctor may make such a schedule by writing, on a so-called "instruction table" sheet for exclusive use, the medical care schedule or plan for the patient such as the schedule and content of the test and the medication, the schedule and content of the medical operation, the schedule and content of the post-operation treatment or examination and so on. As for a medical care record for the medical care actions performed on the basis of the schedule, recording by using an electric medical record is becoming widespread in place of a conventional medical record of a paper or sheet.

Recently, as disclosed in Japanese Patent No. 2706645 (Japanese Patent Application Laying Open NO. Hei 9-185651) corresponding to U.S. Pat. No. 5,913,197 and Japanese Patent No. 2815346 (Japanese Patent Application Laying Open NO. Hei 10-214302) corresponding to U.S. Pat. No. 5,923,018 which have been applied by the present inventor, it is also possible to make such a medical care schedule and a record on a medical care schedule table, in which medical care actions of various types for one patient are arranged in first rows for each type of the medical care actions and in second rows orthogonal to the first rows for each date, displayed on a computer display. Namely, it is possible to make such a medical care schedule and a record on a medical care schedule table which is displayed by executing a program called as a "care map" or on a medical care schedule table which is generally called as a "critical pass", (hereinbelow this kind of medical care schedule table is simply referred to as a "care map" as the occasion demands), by filling each item in the care map in accordance with the diagnosis or observation of the medical doctor More concretely, the medical care schedule maker or recorder such as a medical care doctor sets medical care items related to the pertinent patient as the items to constitute the ordinate (first row) of the table and also sets an appropriate term assigned to the date constituting the abscissa (second row) of the table in which the medical care actions belonging to the set items will be performed, in accordance with the diagnosis or observation, so that the frames of the care map are constructed. Further, he or she inputs the medical care actions to be performed into each frame of the care map at the date and item corresponding thereto (hereinbelow, each frame of the table is called as a "cell" as the occasion demands). Then, after the scheduled medical care action is performed, a performance or result data remains as a confirmed data ill each cell of the care map in place of the schedule data. Namely, in tis care map, the schedule data is shown with the performance or result record data.

According to the above mentioned care map, since the hospital concerned personnel such as the medical doctor, the nurse, the pharmacist etc., who actually performs the medical care schedule, share the performance or result record data and the schedule data, it is possible to make the medical care schedule with little loss and perform the medical care schedule while appropriately adjusting or amending it in cooperation with each other e.g., inputting and changing the data associated with each cell (or each item) in the care map at each of the terminals with reference to required result data as the occasion demand.

Especially, according to the research of the prevent inventors, it is ideal, for making an appropriate medical care schedule for each patient, to deal with a performance or result record data on one patient on the care map not only by a unit of one hospitalization, but also by an unified unit of a plurality of hospitalizations or a plurality of attendances to a hospital or hospitals, and further by a long term such as a decade and ultimately by a patient's life, if they are possible, because the clinical history of the patient can be referred to upon making the schedule. In this case, it is more ideal to deal with the result data on the same patient on the same care map not only at one health care facility such as one hospital, but also at a plurality of health care facilities to which the same patient has attended.

However, according to the above mentioned care map, under the actual scene of the recent sophisticated and complicated medical care, inputted electronic data i.e., medical information is quite various and accumulated data related to the same care map have basically increased.

Especially, as one patient's term which should be treated with the above mentioned care map becomes long, the accumulated data related to the care map become vast. Also, as the health care facilities for one patient which should be treated with the same care map increase in number, the accumulated data related to the same care map become vast.

As a result, in referring to the medical care information on one patient on the above mentioned care map, it becomes extremely difficult for the doctor or the like to find out the exact information on a certain disease to which the doctor or the like would like to refer under each individual concrete circumstance, for example, under the circumstance that a medical care schedule for a patient who has myocardial infarction is being made, even by using a recent scrolling technique or the like. For example, if the care map lists the various information such as medical information recorded in hospitalizing with fracture, medical information on an operation for empyema, diagnosis information on gastric ulcer, a result of visual acuity test, and so on, it becomes extremely difficult to find out the most important medical information on the myocardial infarction on the care map. Moreover, for example, even if the doctor or the like would like to find what the first liver trouble is lie, in making a medical care schedule of a liver trouble for middle-aged, it would be extremely difficult to hunt out the decades-old record on the care map in other medical information on dozens of and hundreds of hospital visits and hospitalizations.

Like the above mentioned, it adversely becomes difficult to achieve the care map's basic object which is to refer to all kinds of medical care information on the care map efficiently, if too much medical information is store. This makes it difficult to deal with the medical care information on one patient as long term as possible and to deal with the information which covers a plurality of medical care facilities on the same care map.

SUMMARY OF THE INVENTION

It is therefore an object of the present invention to provide a system for aiding to make an appropriate medical care schedule and/or record in the form of the table easily, by which it is possible to easily refer to desirable medical care information in dependence upon an individual condition even in case that the volume of medical care information is huge, as well as a program storage device for storing a program such as an information record medium and a computer data signal embodied in a carrier wave, which allow a computer to function as the aiding system.

The above object of the present invention can be achieved by a first system for aiding to make a medical care schedule and/or record provided with: a plurality of files for respectively including medical care data indicating one of a plurality of types of medical care actions, which are set in advance, in correlation with execution timing data indicating an execution timing of respective one of the medical care actions; a display controlling device for (i) generating first display data to display the medical care data composing the medical care schedule and/or record for one patient in a format of a medical care schedule and record table, in which the medical care data are arranged in first rows for each type of the medical care actions and in second rows orthogonal to the first rows for each date, as for only a partial period of a whole period of the medical care schedule and/or record for the one patient, on the bass of the medical care data and the execution timing data included in the files, and (ii) generating second display data to display a table identification mark information, which is to identify the medical care schedule and record table for the one patient, as a patient chronological table exclusive for the one patient in which the table identification mark information is arranged at a position corresponding to the partial period on a time axis indicating the whole period of the medical care schedule and/or record; a display device for displaying the medical care schedule and record table on the basis of the first display data, and displaying the patient chronological table on the basis of the second display data; and a selecting device for selecting one of a plurality of table identification mark information under a condition that the patient chronological table comprising the plurality of table identification mark information is displayed by the display device, the display controlling device taking out one or a plurality of the files storing the medical care data constituting the medical care schedule and record table identified by the table identification mark information selected by the selecting device, to thereby generate the first display data by using the medical care data stored in the taken out file or files.

According to the first system of the present invention, the files respectively include the medical care data indicating one of a plurality of types of medical care actions, such as clinical data, a record of a doctor, a vital sign and so on, in correlation with the execution timing data (i.e., data indicating a time point or a time duration) indicating the execution tiring of respective one of the medical care actions. The medical care schedule and record table comprises a table in which a plurality of the medical care data, which compose the medical care schedule and/or record in the past and/or in the future regarding to one patient, are arranged not for the whole period but for the partial period of the medical care schedule and/or record. For example, it comprises such a table that the date is assigned to the abscissa and the type is assigned to the ordinate or that the date is assigned to the ordinate and the taupe is assigned to the abscissa. A plurality of medical care schedule and record table are respectively identified by the table identification mark information. Namely, the table identification mark information is individually given to each medical care schedule and record table.

At the time of operation, the display controlling device generates the second display data to display the table identification mark information as the patient chronological table exclusive for one patient, in which the table identification mark information is arranged at a position corresponding to the partial period on the time axis indicating the whole period of the medical care schedule and/or recording. Then, the display device displays the patient chronological table on the basis of the second display data. For example, the patient chronological table including a plurality of table identification mark information each shaped mi a bar having a length corresponding to the above mentioned partial period along the time axis, which is prescribed by assigning the date to the abscissa or ordinate may be displayed. Alternatively, the patient chronological table including a plurality of table identification mark information each shaped in a point, which is placed at the position corresponding to the start ting, the end timing or the central timing of the above mentioned partial period, in place of or in addition to the table identification mark information shaped in the bar, may be displayed.

In this manner, under a condition that the patient chronological table, which includes a plurality of table identification mark information, is displayed, a desirable table identification mark information is selected by the selecting device. Then, the display controlling device takes out one or a plurality of the files storing the medical care data constituting the medical care schedule and record table, which is identified by this selected table identification mark information. Then, the display device displays the medical care schedule and record table on the basis of the first display data generated in this manner. Namely, on the basis of the medical care data and the execution timing data respectively stored in a plurality of files, the medical care schedule and record table is displayed, which corresponds to the selected table identification mark information and in which the medical care data are arranged in the first rows for each type and in the second rows for each date, only for the above mentioned partial period regarding to the one patient.

As a result, even if the data volume of the medical care data is huge, it is possible to easily refer to the medical care schedule and record table including the medical care data which is desired to be referred to, depending upon the individual occasions, and it is also possible to deal with the medical information related to a long term in a unified manner.

In one aspect of the first system or in one aspect of the second system of the present invention, the display controlling device generates the first display data to display the medical care schedule and record table as for only part of the types of the medical care actions, and generates the second display data to display the table identification mark information individually for each of the part of the types.

According to this aspect, the medical care schedule and record table is a table in which not all the types of the medical care actions are arranged but only the part of the types of the medical care actions are arranged. Then, a plurality of medical care schedule and record tables are respectively identified by the table identification mark information.

In this manner, under a condition that the patient chronological table, which includes a plurality of table identification mark information, is displayed, a desirable table identification mark information is selected by the selecting device. Then, the display controlling device takes out one or a plurality of the files storing the medical care data constituting the medical care schedule and record table, which is identified by this selected table identification mark information. Then, the display device displays the medical care schedule and record table on the basis of the first display data generated in this manner, Namely, on the basis of the medical care data and the execution timing data respectively stored in a plurality of files, the medical care schedule and record table is displayed, which corresponds to the selected table identification mark information and in which the medical care data are arranged in the first rows for each type and in the second rows for each date, only for the part of the types regarding to the one patient.

As a result, even if the data volume of the medical care data is huge, it is possible to easily refer to the medical care schedule and record table including the medical care data which is desired to be referred to, depending upon the individual occasions, and it is also possible to deal with the medical information related to a long term in a unified manner.

The above object of the present invention can be achieved by a second system for aiding to make a medical care schedule and/or record provided with: a plurality of files for respectively including medical care data indicating one of a plurality of types of medical care actions, which are set in advance, in correlation with execution timing data indicating an execution timing of respective one of the medical care actions; a display controlling device for (i) generating first display data to display the medical care data composing a medical care schedule and/or record for one patient in a format of a medical care schedule and record table, in which the medical care data are arranged in first rows for each type of the medical care actions and in second rows orthogonal to the first rows for each date, as for only part of the types of the medical care actions for the one patient, on the basis of the medical care data and the execution ting data included in the files, and (ii) generating second display data to display a table identification mark information, which is to identify he medical care schedule and record table for the one patient, as a patient chronological table exclusive for the one patient in which the table identification mark information is arranged at a position corresponding to an execution period of the medical care actions of the part of the types on a time axis indicating the whole period of the medical care schedule and/or record; a display device for displaying the medical care schedule and record table on the basis of the first display data, and displaying the patient chronological table on the basis of the second display data; and a selecting device for selecting one of a plurality of table identification mark information under a condition that the patient chronological table comprising the plurality of table identification mark information is displayed by the display device, the display controlling device taking out one or a plurality of the files storing the medical care data constituting the medical care schedule and record table identified by the table identification mark information selected by the selecting device, to thereby generate the first display data by using the medical care data stored in the taken out file or files.

According to the second system of the present invention, the files respectively include the medical care data in correlation with the execution timing data The medical care schedule and record table is a table in which not all the types of the medical care actions are arranged but only the part of the types of the medical care actions are arranged Then, a plurality of medical care schedule and record tables are respectively identified by the table identification mark information.

At the time of operation, the display controlling device generates the second display data to display the table identification mark information as the patient chronological table exclusive for one patient, in which the table identification mark information is arranged at a position corresponding to the period (which may be the whole period or the partial period) as for only part of the types of the medical care actions, on the time axis indicating the whole period of the medical care schedule and/or record. Then, the display device displays the patient chronological table on the basis of the second display data. For example, the patient chronological table including a plurality of table identification mark information each shaped in a bar having a length corresponding to the above mentioned period as for only part of the types of the medical care actions, along the time axis which is prescribed by assigning the date to the abscissa or ordinate may be displayed Alternatively, the patient chronological table including a plurality of table identification mark information each shaped in a point, which is placed at the position corresponding to the start timing, the end tiring or the central timing of the above mentioned period as for only part of the types of the medical care actions, in place of or in addition to the table identification mark information shaped in the bar, may be displayed.

In this manner, under a condition that the patient chronological table, which includes a plurality of table identification marl; information, is displayed, a desirable table identification mark information is selected by the selecting device. Then, the display controlling device takes out one or a plurality of the files storing the medical care data constituting the medical care schedule and record table, which is identified by this selected table identification mark information. Then, the display device displays the medical care schedule and record table on the basis of the first display data generated in this manner. Namely, on the basis of the medical care data and the execution timing data respectively stored in a plurality of files, the medical care schedule and record table is displayed, which corresponds to the selected table identification mark information and in which the medical care data are arranged in the first rows for each type and in the second rows for each date, only for the part of the types regarding to the one patient.

As a result, even if the data volume of the medical care data is huge, it is possible to easily refer to the medical care schedule and record table including the medical care data which is desired to be referred to, depending upon the individual occasions, and it is also possible to deal with the medical information related to a long term in a unfed manner.

In another aspect of the first system or in one aspect of the second system of the present invention, the system is further provided with a magnified portion specifying device for specifying one portion of the patient chronological table as a portion to be magnified under a condition that the patient chronological table is displayed by the display device, the display controlling device generates the second display data to magnify and display the one portion of the patient chronological table specified by the magnified display portion specifying device.

According to this aspect, when one portion of the patient chronological table displayed by the display device is specified by the magnified portion specifying device such as a mouse, a keyboard or the like, this specified portion is magnified. Therefore, in case that a plurality of table identification mark information finely exist on the displayed patient chronological table, or in case that a large number of table identification mark information east adjacent to each other, it is possible to visually and easily recognize what kind of table identification mark exists (i.e., what kind of medical care schedule and record table exist) on the magnified and displayed patient chronological table.

In another aspect of the first or second system of the present invention, the display controlling device generates the second display data to display text information given to respective one of the table identification mark information at a position adjacent to the respective one of the table identification mark information in the patient chronological table.

According to this aspect, since the text information indicating the title, the period or term and the like of the medical care schedule and record table inputted by the doctor etc., (e.g., a title such as "○○ clinic" for each medical care facility, a title such as "X X disease" for each disease) is displayed at the position adjacent to the corresponding table identification mark information, it is possible to visually and easily recognize what kind of table identification mark exists i.e., what lid of medical care schedule and record table exists).

In another aspect of the first or second system of the present invention, the system is further provided with a pop-up specifying device for specking one of the displayed plurality of table identification mark information as one to be pop-up-displayed, under a condition that the patient chronological table including the plurality of table identification mark information is displayed by the display device, the display controlling device generating the second display data to pop-up-display detail information given to the table identification mark information specified by the pop-up specifying device at a position adjacent to the table identification mark information specified by the pop-up specifying device in the patient chronological table.

According to this aspect, when one of a plurality of table identification mark information displayed in the patient chronological table is specified as one to be-pop-up displayed, by the pop-up specifying device such as a mouse, a keyboard or the like, the detail information given to this specified table identification mark information (e.g., a comment of a doctor etc., which is automatically appended or text-inputted, text information indicating the term of the pertinent medical care schedule and record table etc.,) is pop-up displayed at the position adjacent to this table identification mark information. Thus, it is possible to visually and easily recognize what kind of table identification mark information exists (i.e., what kind of medical care schedule and record table exists) on the patient chronological table on which the detail information is pop-up displayed Especially, since the pop-up displayed detail information may be displayed and overlapped on the other portion of the patient chronological table, it is possible to appropriately display the detail information such as text information having a large data volume or the like on the patient chronological table, which is convenient.

In another aspect of the first or second system of the present invention, the display controlling device generates the second display data to display the table identification mark information in a bar shape, which has a length corresponding to a period covered by the medical care schedule and record table identified by the pertinent table identification mark information with respect to the time axis.

According to this aspect, since the start timing and the end timing of each medical care schedule and record table can be expressed on the patient chronological table as the start point and the end point of the table identification mark in the bar shape, it is possible to visually recognize this at a moment notice, which is convenient.

In another aspect of the first or second system of the present invention, the display controlling device generates the second display data to display the table identification mark information in a point shape indicating the date of an execution of one medical care data, which is related to a predetermined type, on the time axis among the plurality of medical care data constituting the medical care schedule and record table identified by the table identification mark.

According to this aspect, since a rough period of each medical care schedule and record table can be expressed by a position of the table identification mark having the point shape on the patient chronological table, it is possible to recognize this rough period at a moment notice, which is convenient. For example, the table identification mark having the point shape may be placed at the position corresponding to a date when a significant medical event occurs such as a medical operation date, a hospitalization date or the like. Alternatively, the table identification mark having the point shape may be placed at the position corresponding to the start timing or the end timing of each medical care schedule and record table.

In this aspect, the display controlling device may generate third display data to display a list of the respective table identification mark information in the point shape and text information given to the respective table identification mark information, the display device displaying the list on the basis of the third display data.

By constructing in this manner, it is possible to visually and easily recognize on the list, to which kind of medical care schedule and record table etc., a plurality of table identification mark information each having the point shape displayed on the patient chronological table are related.

In another aspect of the first or second system of the present invention, the display controlling device generates the second display data so as to add an age of the one patient as well as at least year and month of chronological era as a scale with respect to the time axis.

According to this aspect, since the patient chronological table is displayed by the display device such that the age of the patient as well as at least year and month (and week, day etc., as the occasion demands) is added to the time axis as the scale, it is possible to visually and easily recognize of what time there is the medical care schedule and record table, e.g., of what year AD, what month and what date, or of what age there is the medical care schedule of the patient.

In another aspect of the first or second system of the present invention, the display controlling device generates the second display data to further display a clinical data existence period mark information in the patient chronological table, the clinical data existence period mark information indicating a clinical data existence period, in which clinical data related to one series of clinical actions among the medical care data exist and being shaped in a bar having a length corresponding to the clinical data existence period on the time axis.

According to this aspect, the clinical data existence period mark information is displayed, which is shaped in a bar having the length corresponding to the clinical data existence period on the time axis. The clinical data existence period mark information indicates the clinical data existence period, in which the clinical data related to one series of clinical actions (e.g., the clinical actions with respect one hospitalization or one disease) among the medical care data exist. Therefore, it is possible to visually and easily recognize about when the patient was in the hospital, about when the clinical data of the patient was generated and the like, on the patient chronological table. In addition, at a position adjacent to this clinical data existence period mark information, text information given to this clinical data existence period mark information may be displayed, or detail information given to this clinical data exstence period mark information may be pop-up displayed.

In another aspect of the first or second system of the present invention, the system is further provided with a date and time measuring device for measuring a present date and time, wherein the display controlling device generates the second display data to further display a present date and time mark indicating the measured present date and time within the patient chronological table.

According to this aspect, since the present data and time mark indicating the present data and time measured by the date and time during device (e.g., a mark in a line shape orthogonal to the time axis, a mark in a point shape disposed on the time axis or the like) is displayed in the patient chronological table, it is possible to visually recognize where the present date and time is in the patient chronological table at a moment notice.

In another aspect of the first or second system of the present invention, the system is further provided with a date and time measuring device for measuring a present date and time, wherein the display controlling device generates the first display data to fisher display a present date and time mark indicating the measured present date and time within the medical care schedule and record table.

According to this aspect, since the present data and time mark indicating the present data and time measured by the date and time during device (e.g., a mark in a line shape orthogonal to the time alas, a mark in a point shape disposed on the time axis or the like) is displayed in the medical care schedule and record table, it is possible to visually recognize where the present date and time is in the medical care schedule and record table at a moment notice.

In another aspect of the first or second system of the present invention, the system is further provided with an input device for inputting the medical care data on the medical care schedule and record table.

According to this aspect, the medical care data can be referred to and can be inputted on the medical care schedule and record table, which is very convenient.

In another aspect of the first or second system of the present invention, wherein each of the files comprises an object file for including the medical care data and the execution timing data and further including, procedure information, in accordance with which the display controlling device generates the first display data.

According to this aspect, by means of the so-called object oriented manner, the medical care schedule and record table can be displayed. Alternatively, the medical care schedule and record table may be displayed by means of the agent oriented manner or the like.

In another aspect of the first or second system of the present invention, the system has two units communicated to each other through a communication line, wherein the files are provided in one of the two units, and the display device is provided in another of the two units.

According to this aspect, the files provided in one of the two units and the display device provided in another of the two units are connected to each other through a communication line, such as a wire line, a wireless line, an exclusive line, a general line, a telephone line and so forth. Thus, by preparing the files in a large sized memory device provide in one unit as a center unit, and by employing such a structure that one or a plurality of other units are arranged as terminal apparatuses, it becomes possible to commonly use or share the same data between the plurality of terminal apparatuses. In addition, the display controlling device may be provided in another of the two units in the same manner as the display device. The date and time measuring device may be provided in either one of the two units.

The above object of the present invention can be also achieved by a first program storage device readable by a computer. The first program storage device stores a program of instructions to cause the computer to function as at least one portion of the above described first system of the present invention (including its various aspects).

According to the first program storage device, such as a CD-ROM, a ROM, a DVD, a floppy disk or the like, of the present invention, the above described first system of the present invention can be realized as it reads and executes the program of instructions.

The above object of the present invention can be also achieved by a second program storage device readable by a computer. The second program storage device stores a program of instructions to cause the computer to function as at least one portion of the above described second system of the present invention (including its various aspects).

According to the second program storage device, such as a CD -ROM, a ROM, a DVD, a floppy disk or the like, of the present invention, the above described second system of the present invention can be realized as it reads and executes the program of instructions.

The above object of the present invention can be also achieved by a first computer data signal embodied in a carrier wave and representing a series of instructions for a computer. The series of instructions causes the computer to function as at least one portion of the above described first system of the present invention including its various aspects).

According to the first computer data signal embodied in the carrier wave of the present invention, as the computer downloads the program in the computer data signal through a computer network or the like, and executes this program, it is possible to realize the above described first system of the present invention.

The above object of the present invention can be also achieved by a second computer data signal embodied in a carrier wave and representing a series of instructions for a computer. The series of instructions causes the computer to function as at least one portion of the above described second system of the present invention (including its various aspects).

According to the second computer data signal embodied in the carrier wave of the present invention, as the computer downloads the program in the computer data signal through a computer network or the like, and executes this program, it is possible to realize the above described second system of the present invention.

The nature, utility, and further features of this invention will be more clearly apparent from the following detailed description with respect to preferred embodiments of the invention when read in conjunction with the accompanying drawings briefly described below.

BRIEF DESCRIPTION OF TEE DRAWINGS

FIG. 1 is a block diagram of a system for aiding to make a medical care schedule and/or record as a first embodiment of the present invention;

FIG. 2 is a plan view showing one example of a layer map which is graphically outputted by the first embodiment;

FIG. 8 is a table showing a generation condition master of the layer map in the second embodiment;

FIG. 12 is a conceptual diagram of another operation of a system for aiding to make a medical care schedule and/or record as a forth embodiment of the present invention;

DETAILED DESCRIPTION OF THE PREFERRED EMBODIMENTS

Figure 3:
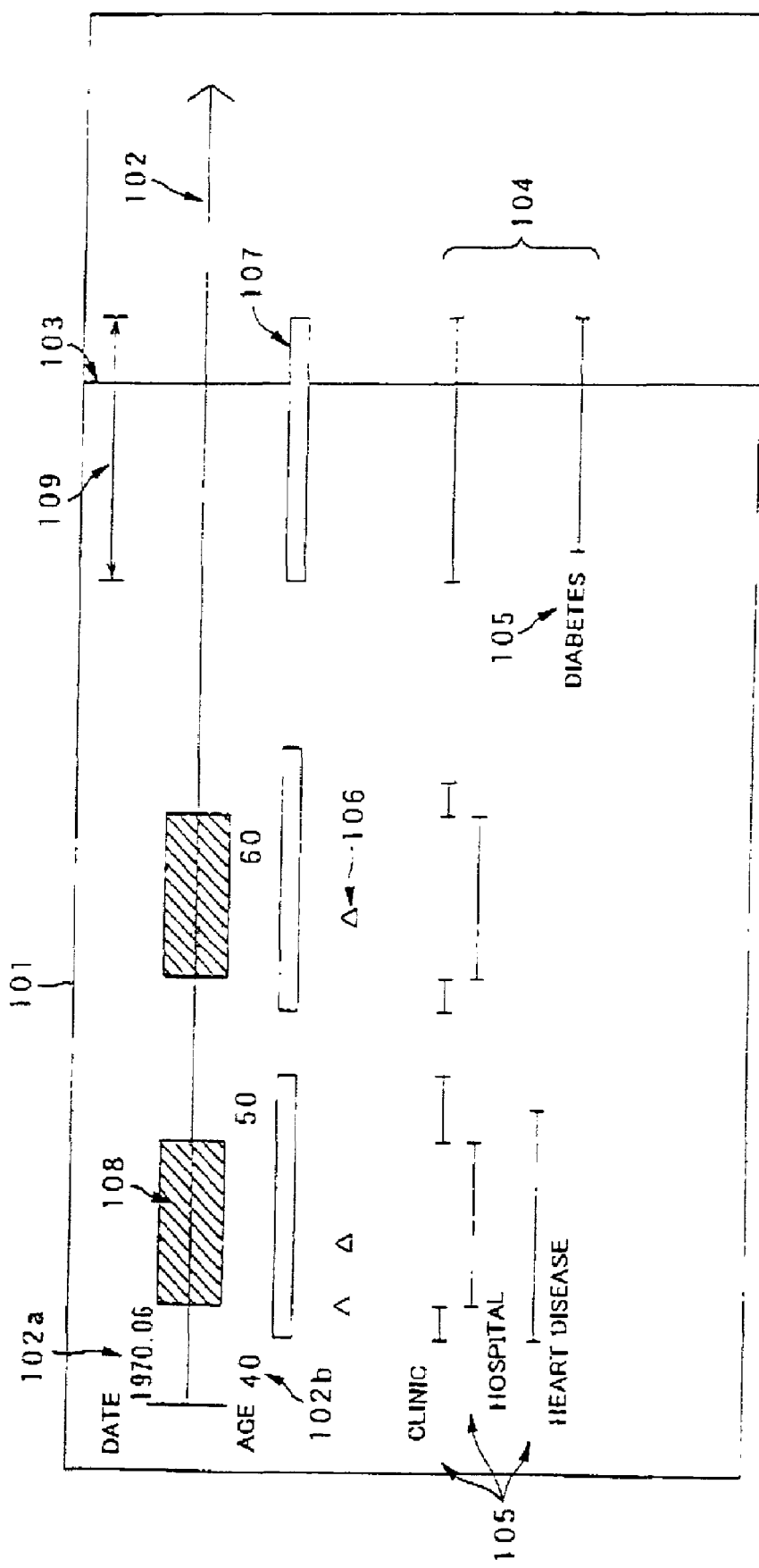
FIG. 3 is a plan view showing one example of a life chart which is displayed on a picture plane of the display device in the first embodiment.

Referring to the accompanying drawings, embodiments of the present invention will be now explained.

(I) First Embodiment

FIG. 1 is a block diagram of a system for aiding to make a medical care schedule and/or record as a first embodiment of the present invention.

In FIG. 1, a system 1 for aiding to make a medical care schedule and/or record may consist of, as a hardware resource, a personal computer, a work station, a middle size computer, a large size computer, a mobile computer (i.e., a hand-carry type information terminal), an electronic diary or the like, and is provided with a memory device 2; an input device 3, a process device 4; a display device 5; a printer 6; a communication device 7; a read device 8; and a system dock 9.

The memory device 2 is preferably a known large data volume memory device of randomly accessible type, such as a hard disc device, an IC (Integrated Circuit) memory, a magnetic disc device, a magneto-optical disc, an optical disc device or the like.

In the memory device 2, there are constructed a plurality of first object files 21, each including: medical care data indicating either one of a plurality of types of medical care actions, which are set in advance, in association with execution timing data indicating execution timing of respective one of the medical care actions.

The first object file 21 Per includes, in addition to the medical care data and the execution timing data, at least one portion of procedure information, in accordance with which the process device 4 generates first display data to display a layer map (refer to FIG. 2) i.e., a medical care schedule and/or record table related to a partial term of one life of each patient and also related to partial kinds of medical care actions, and generates second display data to display a life chart (refer to FIG. 3) i.e., an example of a chronological table of each patient, as described later In the memory device 2, there is also constructed a second object file 31 including procedure information, in accordance with which the process device 4 refers to a present date and time of the system dock 9, calculates a present date and time position in the layer map, calculates procedure information to display a present date and time mark in the layer map, calculates a present position in a life chart, and displays a present mark (which is a mark to display a present date and time) in a life chart as described later. In this manner, the first display data, the second display data or the like can be generated efficiently by virtue of the object file i.e., by using various procedure information stored in the first object file 21 and the second object file 31, in the present embodiment.

Alternatively, without using the first object file 21 and the second object file 31, those kinds of procedure information may be stored in a program file, which is constituted separately from the medical care data and the execution timing data, and are to be executed as the occasion demand. Also, format information prescribing the frame of the table among first display data to display the layer map may be stored in a format information file separately from the first object file 21 and may be read out as the occasion demand, while the procedure information to determine in which cell (surrounded by the frame) the respective medical care data is to be displayed may be stored in the first object file 21.

The input device 3 is provided with a key board, a ten key switch, a mouse, a track ball, an input pen, an input tablet or the like, and is adapted to input the medical care data and the execution timing data as well as other various data or commands, and is further adapted to specify or designate an arbitrary position on the image, especially on the layer map and on the life chart, displayed on the display device 5.

The process device 4 has a CPU (Central Processing Unit) as an example of display control device.

The process device 4 is constructed to generate the first display data to display the layer map refer to PIG 2) as for one patient on the basis of the medical care data, the execution timing data, and the procedure information stored in the first object file 21. Further, the process device 4 is constructed to select one of a plurality of kids of condition marks set in advance in correspondence with the relationship between the present date and time measured by the system clock 9 and the execution timing of the respective one of the medical care actions, according to the procedure information stored in the first object file 21, and to generate the first sub display data to display the selected condition mark such that the selected condition mark is superimposed on or displayed at the vicinity of the corresponding medical care data within the displayed layer map. Moreover, the process device 4 is constructed to calculate a present date and time position within the layer map corresponding to the present date and time measured by the system clock 9, in case that the width of one date in the layer map is converted into 24 hours, and generate the second sub display data to display the present mark, which is set in advance, at the calculated present date and time position.

The process device 4 is further constructed to generate the second sub display data to display a layer bar, as one example of the table identification mark information individually given to each layer map (refer to FIG. 2), placed in the life chart (refer to FIG. 3) at the position corresponding to the partial term related to the corresponding one of the layer maps. Moreover, the input device 3 is constructed to function as one example of the selecting device. Namely, if the input device 3 chooses one of a plurality of the displayed layer bars while the display device 5 displays the life chart in which a plurality of layer bar are included, the process device 4 takes out the object file 21 from the memory device 2 and generates the first display data to display the layer map by using the medical care action data which are stored in the taken out object file 21. Here, the object fie 21 stores the medical care action data, which make up the layer map which is identified by the selected layer bar. In addition, the process device 4 is constructed to calculate a present position corresponding to the present date and time measured by the system clock 9 on the time axis of the life chart, and to generate the second sub display data to display the present mark, which is set in advance, at the calculated present date and time position, according to the procedure information stored in the first object file 21.

The display device 5 may be a known display device such as a CRT (Cathode Ray Tube) display device, an LCD (Liquid Crystal Display) device or the like, is constructed to display the layer map (refer to FIG. 2) on the basis of the first display data generated by the process device 4, and is constructed to display the life chart (refer to FIG. 3) on the basis of the second display data generated by the process device 4. Also, the display device is constructed such that an arbitrary position on its picture plane (i.e., on the layer map and on the life chart) can be designated by the input device 3.

The printer 6 may be a known printer such as a laser beam printer, an ink jet printer or the like, and may be a color type or a black and white type. The printer 6 is constructed to print an arbitrary picture plane displayed on the display device 5 (e.g., the layer map, the life chart, or the like) by inputting a predetermined printing command through the input device 3.

The communication device 7 is provided with a modem etc., to perform a data communication of various files including the first object files 21 and data with another computer or the like. The communication device 7 is connected with other large size computer, personal computer, mobile computer i.e., a hand-carry type information terminal), an electronic diary and the like, through a communication line, such as a wire-line, a wireless line, an exclusive line, a general line, a telephone line and so on.

The reading device 8 may include a CD-ROM drive, a DVD-ROM drive and an FD (Floppy or Flexible Disk) drive for reading a computer program recorded on a record medium 8a, such as a CD-ROM, a DVD-ROM and an FD respectively, for example. The computer program read in this manner allows the computer i.e., the hardware resource of the system 1 to function as the system for aiding to make the medical care schedule and/or record The aiding system may be constructed such that computer programs in those kind axis downloaded by the communication device 7 through communication manner such as Internet or the like, as the carrier transmitted from external servers carries the computer programs, in place of or in addition to reading the computer programs from the record medium 8a.

One or whole portion of the first object files 21 and the second object file 31 constituted in the memory device 2 may be recorded on the record medium 8a, and may be read out as the occasion demand. Especially, it is convenient later to store in advance (i) the first object files 21, which are used for a standard medical care schedule at a stage before mug an individual medical care schedule for a specific patient, or (ii) the standard object files 21, from which as the base the individual medical care schedule can be modified or changed, to the record medium 8a together with the computer program since they can be produced at the time of producing the computer program and since their flexibility is high.

The system dock 9 has a calendar function and always measures the present date and time regardless of the on/off of the main power of the system 1. The process device 4 refers to the date and time measured by the system clock 9 when updating the present mark and the condition mark within the layer map or at a constant cycle. The system 1 may be constructed such that the process device 4 refers to a present date and time signal of a clock device, which is installed at the external of the system 1 and which outputs the present date and time signal indicative of the present date and time at the constant cycle, in place of the system clock 9, to thereby obtain the present date and time.

Next, one example of the layer map, which is displayed on the display device 5 on the basis of the first display data generated by the process device 4, is shown in FIG. 2.

As shown in FIG. 2, the medical care data is displayed on the display device 5 by a format of a layer map 10, in which date is set on an abscissa 12 (i.e., a horizontal axis) while the type of the medical care action is set on an ordinate 11 (i.e., a vertical axis). In this case, while displaying the layer map 10, a condition mark 201 indicative of an execution condition of the respective one of the medical care actions is displayed, and also a present mark 202 indicative of a present date and time position under a condition that the width of one day of the date field (i.e., the horizontal axis) is converted into 24 hours is displayed. The condition mark 201 indicates the execution condition as for the medical care data, which is text-displayed and on which the condition mark 201 is superimposed or at the vicinity of which the condition mark 201 is displayed, by the shapes and/or colors thereof.

In the present embodiment, the "types of medical care actions" mainly text-displayed within the layer map 10 shown in FIG. 2, are the medical care actions categorized in accordance with a hierarchy category system comprising large categories and small categories belonging to each large category. For example, as the large categories, there are "record by doctor or nurse", "process", "injection", "examination", "test", "evaluation", "medication", "meal (food)", "practice", "monitor", "treatment", "activity restriction", "observation", "rehabilitation", "coordination", "hospitalization and leave of hospital", "education for family of patient" and so on. For example, as the small categories belonging to the large category "examination", there are "chest X-ray (photographing)", "head X-ray (photographing)", "electrocardiogram", "body temperature (measurement)", "blood analysis", "urine analysis" and so on.

Incidentally, in the system 1 for aiding to make medical care schedule and/or record in the present embodiment, it is possible to display a medical care schedule and/or record table which includes whole medical care data on the whole period of one patient and on all types of medical care actions. A medical care schedule and/or record table in this lid is called as "a life map" in the present specification. The life map can be practically displayed by using scrolling technique and the like, even within a limited picture plane of the display device 5. Although the displayed picture plane may be similar to the layer map 10 in FIG. 2, the abscissa 12 (i.e., the horizontal axis) and the ordinate 11 (i.e., the vertical axis) increase in length, generally. The layer map 10 will be explained such that "the life map" in this kind exists venally and an extract of one portion of the life map (i.e., one portion related to a partial term and/or one portion related to partial types of the medical care actions) displayed on the display device 5 corresponds to the layer map 10 in FIG. 2.

As shown in FIG. 2, the lines each dividing the types of the medical care actions in the layer map 10 are lines to divide the large categories such as "examination", "recordings" and so on. If there are a plurality of medical care data, which are performed on the same day or belong to the same large category, they are arranged within one cell 10a in the layer map 10. How to set the column of the types based on the large categories on the ordinate 11 of the layer map 10 may be fixed or the medical care schedule and/or record maker such as the medical doctor may freely set the column of the types of the layer map 10 in harmonization with the medical care schedule and/or record for the respective one of the patients.

The "medical care data" which are mainly text displayed in the layer map 10 shown in FIG. 2 may be schedule data and/or result data showing a medical care action just scheduled by the medical care schedule and/or record maker (e.g., the schedule is still being considered in relation to other patients or other medical care actions constituting the one series of medical care schedule, so that any action other than inputting the information for the pertinent medical care action is not performed yet), a medical care action whose order is issued (e.g., an order instructing the medicine distribution or the reservation for a specific examination has been issued to a computer in other departments such as the medicine department or the examination department through the ordering system), a medical care action to be urgently performed (e.g., the schedule timing is today or tomorrow), may be a medical care action which has been already performed, a medical care action to be continuously performed (e.g., in a condition that the treatment is continuously performed by an artificial respiration device), a medical care action to be periodically performed during a predetermined time duration (e.g., in a condition to perform medication 6 times per day continuously for 3 days), a medical care action which has been scheduled but has never been performed, may be a medical care action to be performed as the occasion demands (e.g., a specific treatment is to be applied if a certain vital sign exceeds a critical value or a spasm occurs), and so on.

Those kind of medical care data may be inputted one by one for each medical care action composing one series of medical care schedule, so that the first object file 21 may be newly registered or its content may be changed Those medical care data may be inputted through an input picture plane for the medical care data, which is window displayed, in a condition that the layer map 10 is displayed by the display device 5. Those medical care data may be inputted from another system, which connects to the system 1 by a computer network, through the communication device 7. Alternatively, by an inputting operation through the read device 8 such as the hard disc, the floppy disc, or the like, the medical care data related to a plurality of medical care actions composing one series of medical care schedule corresponding to the patient name (the patient code), the disease name (the disease code), the patient attribute (the patient attribute code) and so on may be specified at once.

Then, the "execution timing data" indicative of the execution timing of the medical care action indicated by the medical care data in those kinds is the data indicative of each execution timing (e.g., an execution timig in the past, at the present or in the future, on the result base or on the schedule base) e.g., one time, a plurality of times, periodically, continuously, continually, as the occasion demand and so on. Those kinds of execution timing data may be inputted through the input device 3 etc., by directly inputting a certain date and time or a certain period in the same manner as the above mentioned inputting operation for the medical care data. However, in the present embodiment, this inputting operation is advanced such that the execution timing data is registered to the first object file 21 by automatically setting the respective execution timings of the medical care actions composing one series of medical care schedule, with considering the mutual relationships between those medical care actions and by using an appropriate standard date, in accordance with the setting procedure information stored in the first object file 21 as described later.

Figure 4:
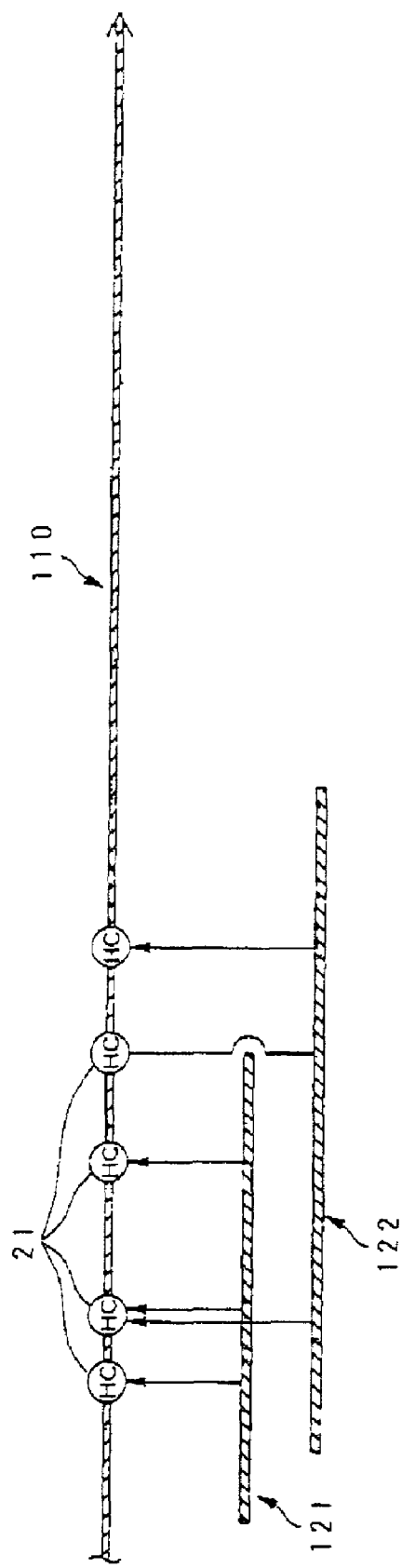
FIG. 4 is a schematic diagram showing a structure of the layer map in the first embodiment.

Next, the life chart i.e., an example of a chronological table for each patient is explained with reference to FIG. 3 and FIG. 4. FIG. 3 is a plan view of the life chart which is displayed on a picture plane of the display device and FIG. 4 is a schematic diagram showing a structure of the layer map with reference to a life map.

As shown in FIG. 3, a life bar 102 extending horizontally on a picture plane (extending left to right as time goes by) which expresses a life of one patient is displayed as one example of time axis on a life chart 101. On the life bar 102, a scale of the date (e.g., year, month and date) 102a and a scale of the patient's age 102b are given.

A present mark 103 which is perpendicular to the life bar 102 (which extends vertically on a picture plane) is displayed such that the mark crosses the corresponding position to the present date (the present time) on the life bar 102, on the basis of the measure result by the system clock 9 (refer to FIG. 1). The life bar 102 in those kind relatively moves right as the time proceeds e.g. by the unit of an hour, a day or a week.

A layer bar 104 which is an example of the table identification mark information showing the presence of the layer map 10 is displayed on the basis of the scale of the life bar 102. Therefore, the layer bar 104 expresses the start timing and the end timing of corresponding each layer map as the starting point (the left endpoint) and the end point (the right endpoint) of the bar which extends horizontally on the life chart 101. A plurality of layer bars 104 are arranged on different rows depending on the kind of corresponding layer map 10. Moreover, a text information 105 indicative of the respective layer map types such as "a clinic", "a hospital", "heart disease" and the like is displayed at vicinity of the respective one of the layer bars 104.

In this manner, if the requested layer bar 104 is chosen by the input device 3, as one example of the selecting device, while the life chart 101 which includes a plurality of layer bars 104 is displayed, the process device 4 takes out the object file 21 in which the medical care data, which constructs the layer map refer to FIG. 2) identified by the selected layer bar 104, are stored and generates the first display data by using it. Then, the display device 5 displays the layer map (refer to FIG. 2) on the basis of the first display data generated as mentioned above.

More concretely, as illustrated in FIG. 4, the layer bar 104 (refer to FIG. 3) has a pointer for the object file (HC) 21 constructing the layer map 121 (or 122) that the layer bar 104 identifies, among all the object files (HC) 21 constructing the life map 110 virtually existing as aforementioned Consequently, if desired one of a plurality of layer bars 104 is chosen by the input device 3, the pointer for the selected layer bar 121 (or 122) is read out. Then, by taking out a plurality of the object file (HC) 21 that the pointer indicates, the layer map 121 (or 122) is taken out as a form of an extract from the life map and is finally displayed as the layer map which relates to one portion of the term and one portion of the kinds of medical care actions as shown in FIG. 2. In FIG. 4, the layer map 121 is the map which, for example, includes the medical care data related to the medical care at the hospital A, and the layer map 122 is the map which, for example, includes medical care data related to the medical care at the hospital B.

Further, it is possible to arbitrarily select display or non-display of the object files (HC) 21 which belong to the respective layer maps 121 (or 122). It is possible to display the layer map 10 by using all of the object files (HC) 21 (refer to 4) which belong to the corresponding the layer map 121 (or 122) when one layer bar 104 is chosen on the life chart 101 (refer to FIG. 3). Alternatively, it is possible to display the layer map 10 by using only one portion of the object files (HC) 21 which belong to the corresponding the layer map 121 (or 122). Moreover, it is possible to choose two layer bars 104 on one life chart 101, and in this case, it is possible to display the object files 21 which belong to the corresponding layer maps 121 and 122, as the layer map 10 merged with AND condition, the layer map 10 merged with OR condition, or the layer map 10 merged with NOT condition.

In FIG. 3 again, an event mark 106, which is another example of a pointer styled table identification mark information, is displayed with respect to the scale of the life bar 102 as the standard The event mark 106 indicates the fact that there exists "event information" indicative of the medically special condition such as recording physically change of a patient, symptoms, comments and the like, for the timing or period corresponding to the position of the event mark 106. Further, it is possible to automatically collect and register this kind of event information. For example, as for important medical care actions related to an operation date, an operative method, a certain disease, and the like, they are set up such that they are automatically collected and registered in advance. Alternatively, it is possible to manually register the event information, for example, when the doctor or the like records the information in which they are really interested. For example, event information such as date of an attack of disease and the like (the first, the n-th, where n: natural number, etc.), the first day the disease begins, the comment in visiting a hospital, and so forth may be registered.

The event information may include various kinds of information such as date, text information or code information indicative of the event content, information indicative of a layer map which relates to the event content, information indicative of object file which relates to the event content, sort cord of event, text or code information indicative of disease, text or code information indicative of symptom, a clinical chart, and so on.

In this case, preferably, a table of the event mark 106 and the text information given to the event mark 106 is displayed with the display device 5, separately from the life chart 101 (e.g., window-displayed on the life chart 101). In this manner, it is possible to confirm to which layer map and the like the respective event marks 106 refer on the table.

The system may be constructed such that the layer map 10 (refer to FIG. 2) corresponding to the event mark 106 is displayed by choosing the event mark 106 with the input device 3, which is the same way as the layer mark 104. For example, the system may be constructed such that, by referring to the date information within the event information corresponding to the selected event mark 106, the layer map 10 related to the term including the date indicated by this date information is displayed (e.g., with this date at the center). Alternatively, the system may be constructed such that, by referring to the disease identification information within the event information related to the selected event mark 106, the layer map 10 related to the medical care action associated with this disease identification information is displayed.

Further, in the present embodiment, a medical care data existence period bar 107 indicative of a range (period) in winch medical care data associated with one series of medical care actions exist is displayed on the life chart 101, with respect to the scale of the life bar 102 as the standard. The medical care data existence period bar 107 is a bar-shaped mark, whose length corresponds to the period for which the medical care data exists, with respect to the life bar 102 as the time axis.

In addition, in the present embodiment, a hospital period bar 108 is displayed overlapped on the life bar 102. The hospital period bar 108, which has the time axis of the life bar 102, is a barshaped mark whose length corresponds to the hospital period. A present map period indication bar 109 indicating the period covering the layer map 10 (refer to FIG. 2), which corresponds to the present is also displayed. The present map period indication bar 109, which has the time axis of the life bar 102, is a bar shaped mark whose length corresponds to the period of the layer map 10 relating to the period including the present.

The present embodiment is constructed such that, if the input device 3 designates the display element such as the layer bar 104, the event mark 106, the medical care data exstence period 107, the hospital period bar 108, the present map period instruction bar 109 and so on, as the display element for pop-up-displaying (for example, if an icon is positioned on the respective display element by using a mouse or the like.) while the life chart 101 is being displayed as shown in FIG. 3, the detailed information given to the designated display element is pop-up-displayed at a vicinity of the designated display element (e.g., the layer bar 104, the event mark 106 etc,). Here, the detailed information is, for example, comment by a doctor or the like, text information indicating the period of the layer map 10, and so on, which may be automatically given or text-inputted.

Moreover, the present embodiment may be constructed such that, by designating one portion of the life chart 101 to display it expansively while the life chart 101 is being displayed, the designated one portion of the life chart 101 is expansively displayed.

As explained above, according to the first embodiment, the life chart 101 including a plurality of the layer bars 104 is displayed first (refer to FIG. 3), and then, the layer map 10 on which medical care action for only one portion of the period and only one portion of the types of medical care actions are arranged by date and by type is displayed. Hence, it is possible to easily refer to the layer map 10 including the medical care data to which one would like to refer depending on individual conditions even if the data volume of the medical care data is enormous Furthermore, it is possible to process long-term medical care data in a united manner.

Incidentally, the above embodiment explains that the layer map 10 is a medical care schedule and/or record table on which medical care actions for only one portion of the period and only one portion of the types of medical care actions are arranged by date and by type. However, it is also possible to constitute the layer map 10 as a medical care schedule and/or record table on which only one portion of the types of medical care actions for the whole period are arranged by date and by type, or, it is also possible to constitute the layer map 10 as a medical care schedule and/or record table on which all the types of medical care actions for only one portion of the period are arranged by date and by type In any case, it is possible to avoid such a disadvantage that the life map is actually displayed on a picture plane of the display device 5.

Figure 5:
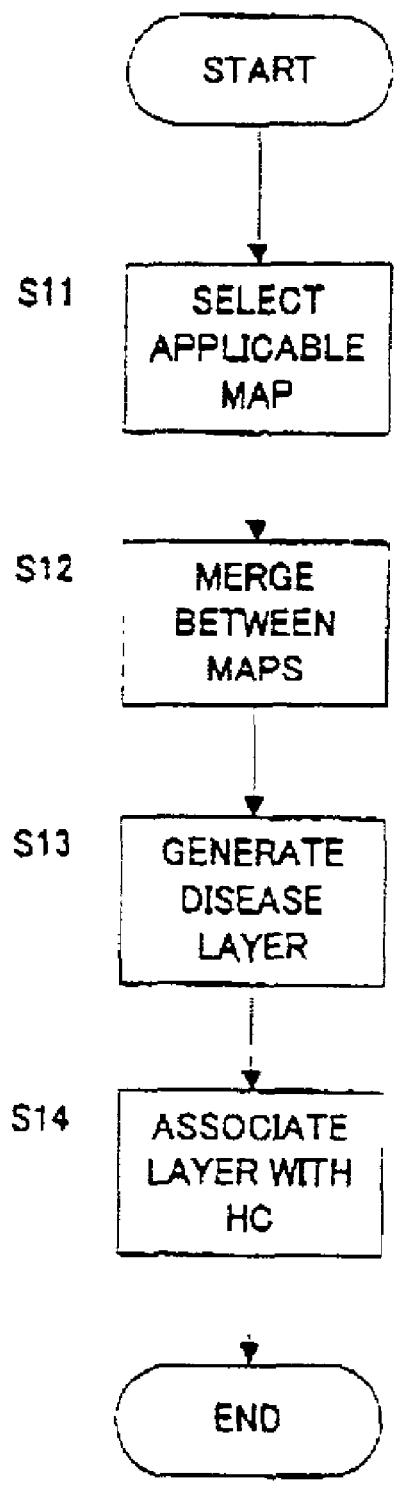
FIG. 5 is a flow chart of a method of generating the layer map in the first embodiment.
Figure 6:
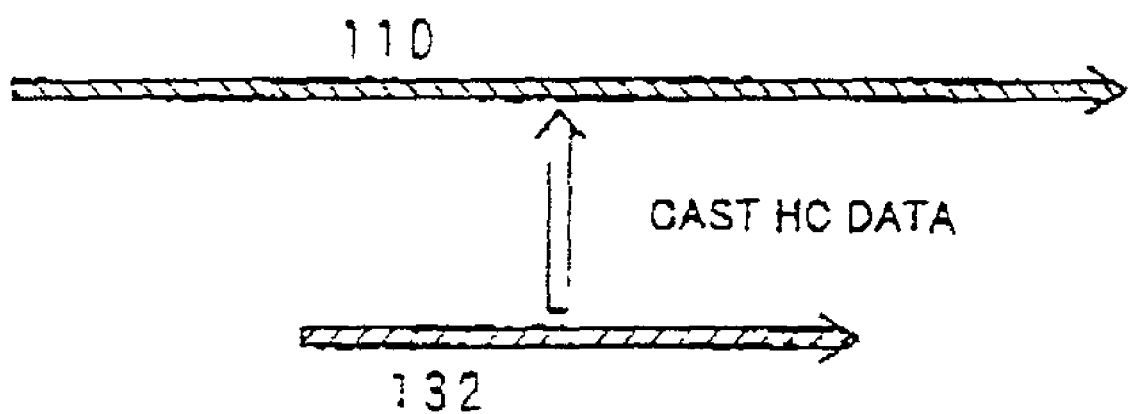
FIG. 6 is a schematic diagram of the method of generating the layer map in the first embodiment.

Next, the generation procedure of the layer map of the first embodiment associated with only one portion of the types and with only one portion of the period is explained with reference to FIG. 5 and FIG. 6 FIG. 5 is a flow chart of a method of generating the layer map of the first embodiment, and FIG. 6 is a schematic diagram of the method of generating the layer map of the first embodiment.

The first embodiment is constructed to prepare for a general purpose template or basic template (which is a portion of a layer map), such as a template separated by diseases, to merge the template to the life map of the patient, and to generate the layer map about the certain disease (namely, to specify the object file 21 which constitutes the required layer map).

Namely, in FIG. 5, at first, a process of selecting the general purpose layer map part or the basic layer map part (i.e., a template for a specific use) applicable for the required layer map is performed (step S11) Then, a process of merging the selected layer map part with the life map 110 of the one patient is performed (step S12). By this, the medical care action type and the timing are determined, so that the layer map as for the required disease is generated (step S13) Further, a process of associating the generated layer map with the object file (HC) 21 is performed, and the generation of the layer map is ended.

For example, as shown in FIG. 6, when a layer map 132 for the heart disease A is to be generated, the object file (HC) 21 which constitutes the layer map 132 is added to the object file 21 belonging to a life map 110 of the pertinent patient.

In the above explained first embodiment, on the life chart 101 shown in FIG. 3, the left side of the present mark 103 corresponds to an area of the past, and the layer map 10 corresponding to the layer bar 104, the event mark 106 and the like, includes the result data recorded in the past as medical care data, mainly. On the other hand, on the life chart 101, the right side of the present mark 103 is an area of the future, and the layer map 10 corresponding to the layer bar 104, the event mark 106 and the like, includes the schedule data which will be done in the future as medical care data, mainly. Therefore, it is also possible to display the life chart 101 such that the right side and the left side of the present mark 103 are displayed in the different form from each other, in the same way that the display form is different on each side of the present mark 202 (e.g., it is possible to change colors or to give different marks).

In addition, preferably, it is possible To constitute the layer map 10, which corresponds to the layer bar 104, the event mark 106 or the like on the right side of the present mark 103 on the life chart 101 shown in FIG. 3, as the layer map 10 relating to a preventive medical care which will be done in the future through patient's life, or as the layer map 10 regarding to a health care schedule or a health promotion schedule. More concretely, it is desirable to generate the layer map 10, which includes medical care data (schedule data) comprising contents of examination which should be done next, examination frequency in the future, living habit instruction in the future, and the like, as a future's layer map. In this case, it is more desirable fist to construct in the memory device 2 or the like a knowledge base indicating the association of patient attributes (e.g., race, sex, age, blood type, family history, etc.) with concrete contents of a health care schedule and the like, and then to generate the layer map 10 and the life chart 101 including the medical care data (schedule data) indicative of the health care schedule corresponding to the each patient attributes with reference to the knowledge base, upon generating each patient's life chart 101 or a layer map 10 in the future. For example, in association with sex simply as attributes (with reference to a table typed knowledge base in which one item of attributes corresponds to one item of examination), the layer map 10 in the future may include medical care data (schedule date) indicative of doing a certain examination item Alternatively, in association with a plurality of attributes such as sex, age, family history, and the like (with reference to a knowledge base in which a plurality of items of attributes correspond to one item of examination according to a certain rule), the layer map 10 may include medical care data (schedule data) indicative of doing a certain examination item.

(II) Second Embodiment

Figure 7:
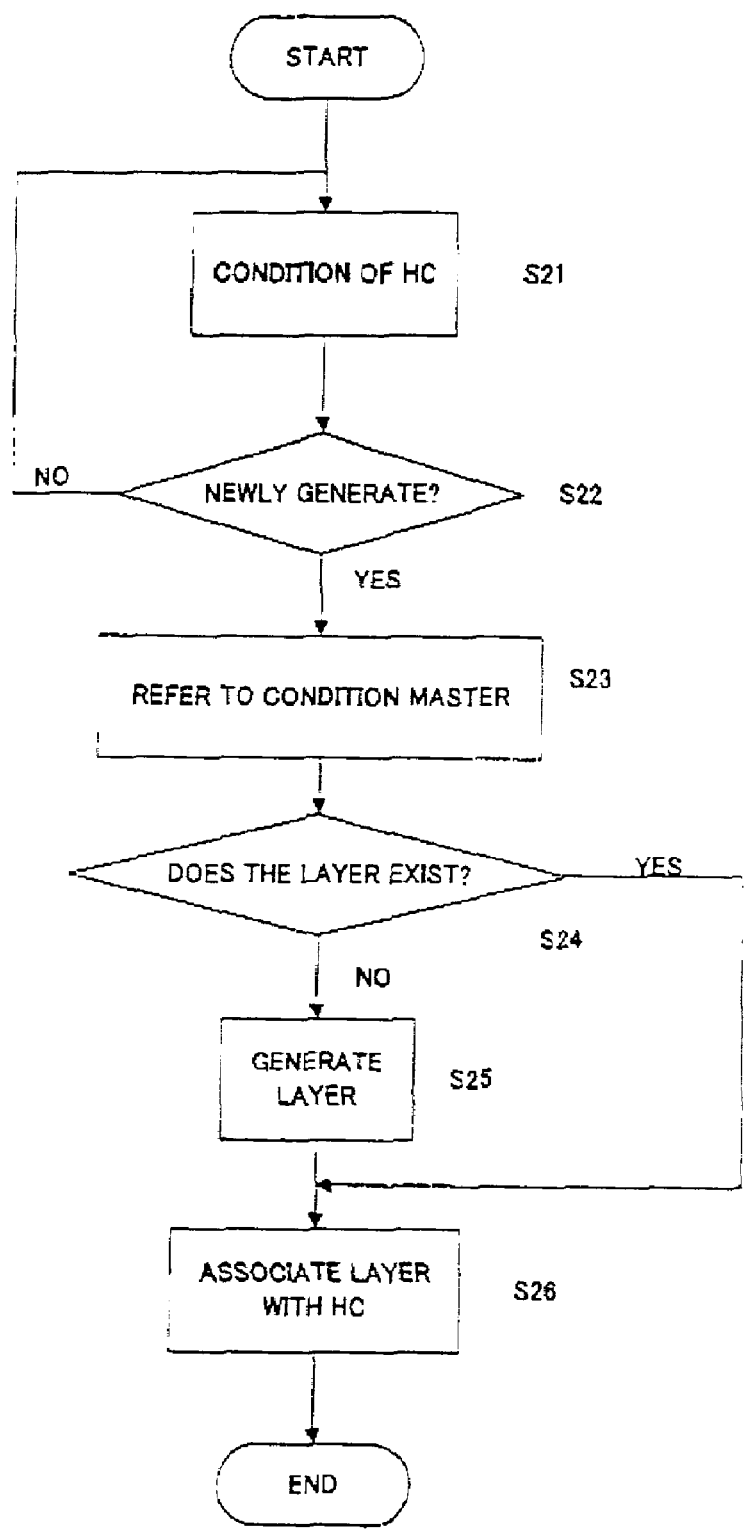
FIG. 7 is a flow chart of a method of generating the layer map in the second embodiment of the present invention.

The second embodiment of the present invention is explained with reference to FIG. 7 and FIG. 8. FIG. 7 is a flow chart of the generation system of the a layer map of the second embodiment, and FIG. 8 is a table showing a generation condition master of the layer map of the second embodiment.

In the second embodiment, the method of generating the layer map is different from that in the first embodiment, but the other features of the second embodiment are the same as those of the first embodiment. Therefore, the method of generating the layer map of the second embodiment is explained here.

In the second embodiment, when the object file 21 is newly made (or when its content is changed), the layer map is automatically generated according to the information such as facilities, clinics, contents written in a clinic chart, etc., included in the medical care data stored in the object 21 (i.e., the object file 21 which constitutes the required layer map is automatically specified).

Namely, in FIG. 7 at first, a condition of the object file (HC) 21 of one patient is checked (step S21). Then, it is monitored whether the object file (HC) 21 is newly generated or not (or, whether the existing object file (HC) 21 has been changed or not) (step S22).

When the object file (HC) 21 is newly generated (step S22: YES), condition master 130 is referred to, as illustrated in FIG. 8 (step S23). For example, when the object file (HC) 21 is generated, if it meets with the condition that the department of a hospital is the internal department for the medical care data included ill the object file (HC) 21, this object file 21 is regarded as the file belonging to a layer map as for the internal department. Alternatively, for example, when the object file (HC) 21 is generated, if it meets with the condition that a facility is a clinic for the medical care data included in the object file (HC) 21, this object file 21 is regarded as the file belonging to a layer map as for a clinic.

Then, it is judged whether the layer map for one patient has already existed or not (step S24). In the case of absence (step S24; NO), after the layer map is generated (step S25), the layer map is associated with the object file 21 (step S26).

On the other hand, if the layer map for one patient has already existed (step S24: YES), the layer map, as it is, is associated with the object file 21 (step S26) Then a series of generation process of a layer map ends.

(III) Third Embodiment

Figure 9:
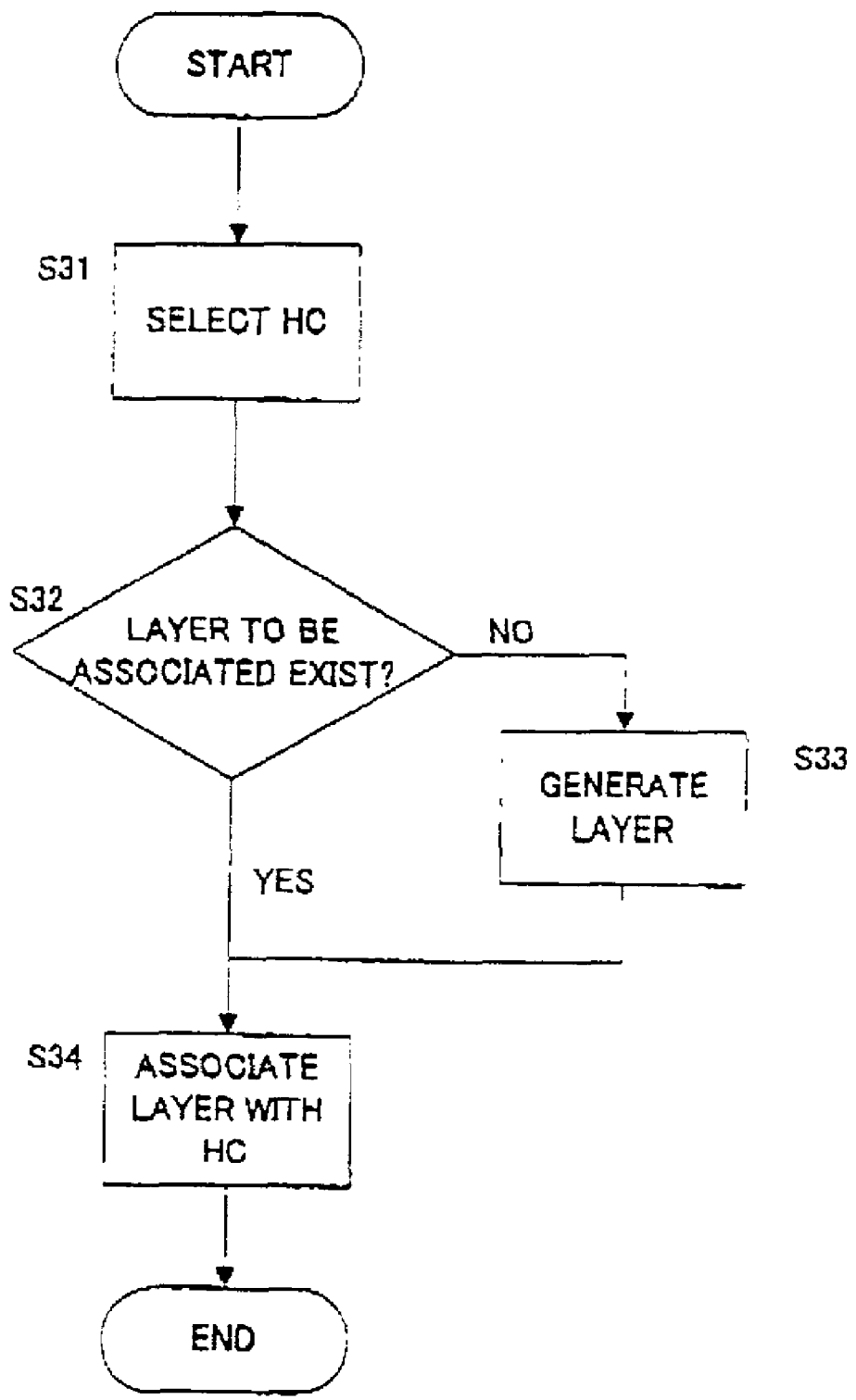
FIG. 9 is a flow chart of a method of generating the layer map in the third embodiment of the present invention.
Figure 10:
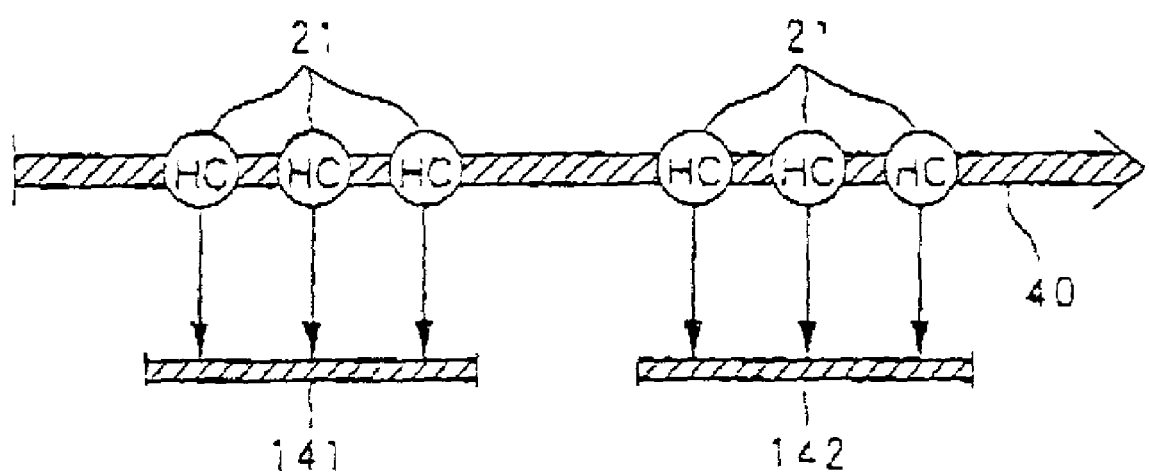
FIG. 10 is a schematic diagram of the method of generating the layer map in the third embodiment.

The third embodiment of the present invention is explained with reference to FIG. 9 and FIG. 10. FIG. 9 is a flow chart of the method of generating the layer map in the third embodiment. FIG. 10 is a schematic diagram of the method of generating the layer map in the third embodiment In the third embodiment, the method of generating the layer map is different from that in the first embodiment, but the other features of the third embodiment are the same as those of the first embodiment. Therefore, the method of generating the layer map of the third embodiment is explained here.

The third embodiment is constructed such that an operator such as a doctor arbitrarily generates a layer or arbitrarily associates the layer with the object files 21, so that the object file 21 can be organized and the object file 21 related with the period of interest can be extracted after the generation of the object file 21 (ie., the object file 21 constituting a required layer map is specified by an external assignment).

Namely, in FIG. 9 firstly, the object file (HC) 21 is selected (step S31), and it is judged whether there is a layer map to be associated with or not (step S32). If there is no layer map to be associated with (step S32. NO), after a layer map is newly generated (step S33), the layer map is associated with this object file (HC) 21 (step S34).

On the other hand, if there is a layer map to be associated with (step S32: YES), the layer map, as it is, is associated with this object file (HC) 21 (step S34). Then a series of generation of the layer map ends.

For example, as shown in FIG. 10, the layer maps of the patient are constructed by such a manner that a doctor or the like arbitrarily associates the first attack layer map 141 and the second attack layer map 142 with the object files (HC) 21 which constitute a life map 140.

(IV) Forth Embodiment

Figure 11:
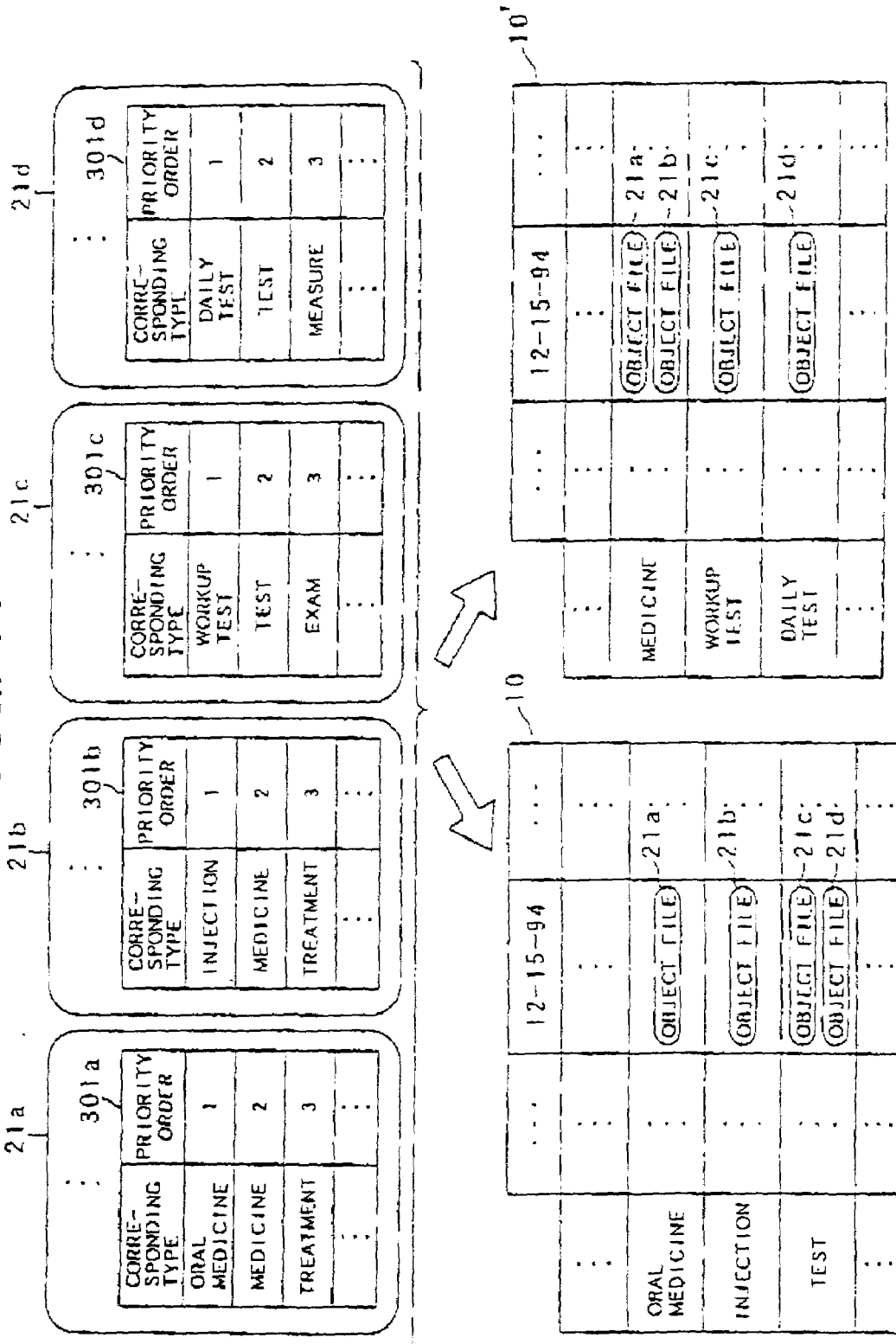
FIG. 11 is a conceptional diagram of one operation of a system for aiding to make a medical care schedule and/or record as a forth embodiment of the present invention.

A forth embodiment of the present invention is explained with reference to FIG. 11 and FIG. 12. FIG. 11 shows one operation of the forth embodiment. FIG. 12 shows another operation of the forth embodiment.

In the above first to third embodiments, it is sometimes difficult to categorize the type of the medical care action. Namely, one action may be categorized into either one of a type A and a type B. Further, one action may be categorized into a type A and may be categorized into a type A', which includes the type A or is included in the type A, depending upon the types composing the layer map, which may be set as a default one or which may be selected or modified by the medical care schedule and/or record maker.

Therefore, in the fourth embodiment, as shown in an upper portion of FIG. 11, the first object files 21a, 21b, 21c, 21d, . . . have multiple correlation information 301a, 301b, 301c, 301d, . . . , respectively. Thus, depending on the types present in the layer map 10 shown in FIG. 2, each of the first object files 21a, 21b, 21c, 21d, . . . finds out to which type the pertinent object file itself is to be corresponding, with referring to the corresponding type data and the priority order data in each multiple correlation information 301. For example, as shown in the upper portion of FIG. 11, the multiple correlation information 301a of the first object file 21a has the corresponding type data and the priority order data indicating that the object file 301a is to belong to the type "oral medicine" with the highest priority (priority No. 1), is to belong to the type "medicine" with the second priority (priority No. 2), is to belong to the type "treatment" with the third priority (priority No. 3) and so on. The multiple correlation information 301b of the first object file 21b has the corresponding type data and the priority order data indicating that the object file 301b is to belong to the type "injection" with the highest priority, is to belong to the type "medicine" with the second priority, is to belong to the type "treatment" with the third priority and so on. The multiple correlation information 301c of the first object file 21c has the corresponding type data and the priority order data indicating that the object file 301c is to belong to the type "workup test" with the highest priority, is to belong to the type "test" with the second priority, is to belong to the type "examination" with the third priority and so on. The multiple correlation information 301d of the first object file 21d has the corresponding type data and the priority order data indicating that the object file 301d is to belong to the type "daily test" with the highest priority, is to belong to the type "test" with the second priority, is to belong to the type "measure" with the third priority and so on.

Accordingly, in case that a layer map 10 shown in a lower left portion of FIG. 11 is currently displayed, i.e., the types "oral medicine", "injection" and "test" are present in the type column of the layer map 10, the first object file 21a is correlated with the "oral medicine" type according to the priority order data of the multiple correlation information 301a (indicating that the highest priority is given to the "oral medicine"). In this case, the first object file 21b is correlated with the "injection" type according to the priority order data of the multiple correlation information 301b indicating that the highest priority is given to the "injection"). In this case, the first object file 21c is correlated with the "test" type according to the priority order data of the multiple correlation information 301c (indicating that the second priority is given to the "test") while the "workup test" type to which the highest priority is given by the multiple correlation information 301c is not present in the layer map 10. Further in this case, the first object file 21d is correlated with the "test" type according to the priority order data of the multiple correlation information 301d (indicating that the second priority is given to the "test") while the "daily test" type to which the highest priority is given by the multiple correlation information 301d is not present in the layer map 10.

On the other hand, in case that a layer map 10' shown in a lower right portion of FIG. 11 is currently displayed, i.e., the types "medicine", "workup test" and "daily test" are present in the type column of the medical care schedule table 10', the first object file 21a is correlated with the "medicine" type according to the priority order data of the multiple correlation information 301a. In this case, the first object file 21b is correlated with the "medicine" type according to the priority order data of the multiple correlation information 301b. In this case, the first object file 21c is correlated with the "workup test" type according to the priority order data of the multiple correlation information 301c. Further in this case, the first object file 21d is correlated with the "daily test" type according to the priority order data of the multiple correlation information 301d.

In this manner, according to the forth embodiment, it is possible to correlate respective one of the first object files 21a, 21b, 21c, 21d, . . . , to the appropriate type on the basis of the multiple correlation information 301a, 301b, 301c, 301d, . . . , even in case that the types present in the layer map are not fixed but are changed in various manners in favor of the medical care schedule and/or record maker such as a doctor.

In addition, if there exists any object file which cannot find to which type the object file itself is to belong, an error message indicating the fact may be outputted. Alternatively, the present embodiment may be constructed such that an operation of automatically re-formatting the layer map to make a room (i.e., a new type column) for the pertinent object file in the currently displayed layer map may be performed according to the multiple correlation information of the object files.

Furthermore, the present embodiment may be constructed such that an operation of automatically re-formatting the layer map to omit or thin out a row for a type, with which any one of the object files is not correlated, in the currently displayed layer map is performed according to the multiple correlation information 301 (refer to FIG. 11) or the medical care data of the first object files 21.

Namely, as shown in an upper portion of FIG. 12, if an empty row exists (i.e., each of the row for the "injection" and the row for the "rehabilitation" is empty) in the layer map 10, the empty row is thinned out by the automatic re-formatting operation according to the first object file 21, so that a layer map 10' in which no empty row eats is displayed as shown in a lower portion of FIG. 12. Thus, it is possible to efficiently see the layer map 10' within a limited vision of the display device.

In the same manner, if an empty column exists in the layer map 10, the empty column may be thinned out by the automatic reformatting operation according to the first object file 21, so that the medical care schedule table in which no empty column exists may be displayed.

(V) Fifth Embodiment

An fifth embodiment of the present invention is explained with reference to FIG. 13.

Figure 13:
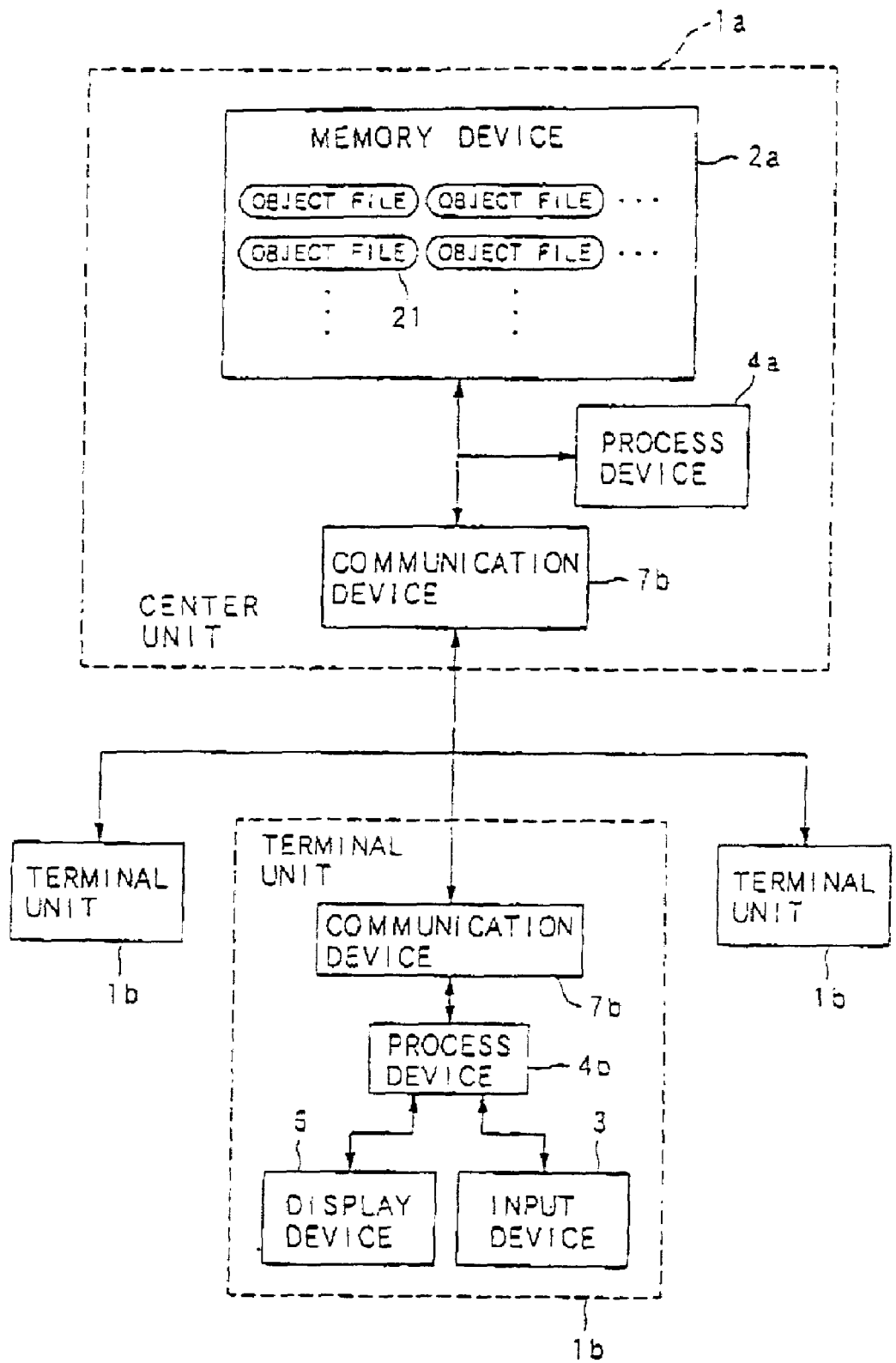
FIG. 13 is a block diagram of a system for aiding to make a medical care schedule and/or record as a fifth embodiment of the present invention.

In FIG. 13, the system for aiding to make the medical care schedule and/or record as the fifth embodiment is provided with a plurality of units communicated through the transmission line. A plurality of first object files 21 are provided on the side of a center unit 1a, while the input device 3, the process device 4a, the display device 5 and the communication device 7a are provided on the side of each terminal unit 1b. The center unit 1a is provided with a large size computer, a host computer or a server; and a large size memory device 2a for storing the first object files 21. The terminal unit 1b is provided with a personal computer, a work station, a mobile computer (i.e., a hand carry type information terminal), an electronic diary or the like. Further, (i) the first object files 21 stored in the memory device 2a of the center unit 1a and (ii) the input device 3, the process device 4a and the display device 5 provided on the terminal unit 1b are coupled through a communication line, which may be a wire-line, a wireless-line, an exclusive line, a general line, a telephone line or the like. Therefore, by virtue of such a structure that the plurality of first object files 21 are stored in the large size memory device 2a equipped on the center unit 1a and that a plurality of terminal units 1b are arranged, it is possible to commonly use the same data by a plurality of terminal units 1b. In such a structure, the process device 4 may be equipped on the center unit 1a or the terminal unit 1b as illustrated by the process devices 4a and 4b. According to the present embodiment, a plurality of object files 21 or data sets stored in the memory device 2a of the center unit 1a can be commonly used, and it is not necessary to equip a large size memory device, which has a capacity enough to store a large number of first object files 21, on each terminal unit 1b, which is advantageous in a practical sense.

(X) Function of System

Figure 14:
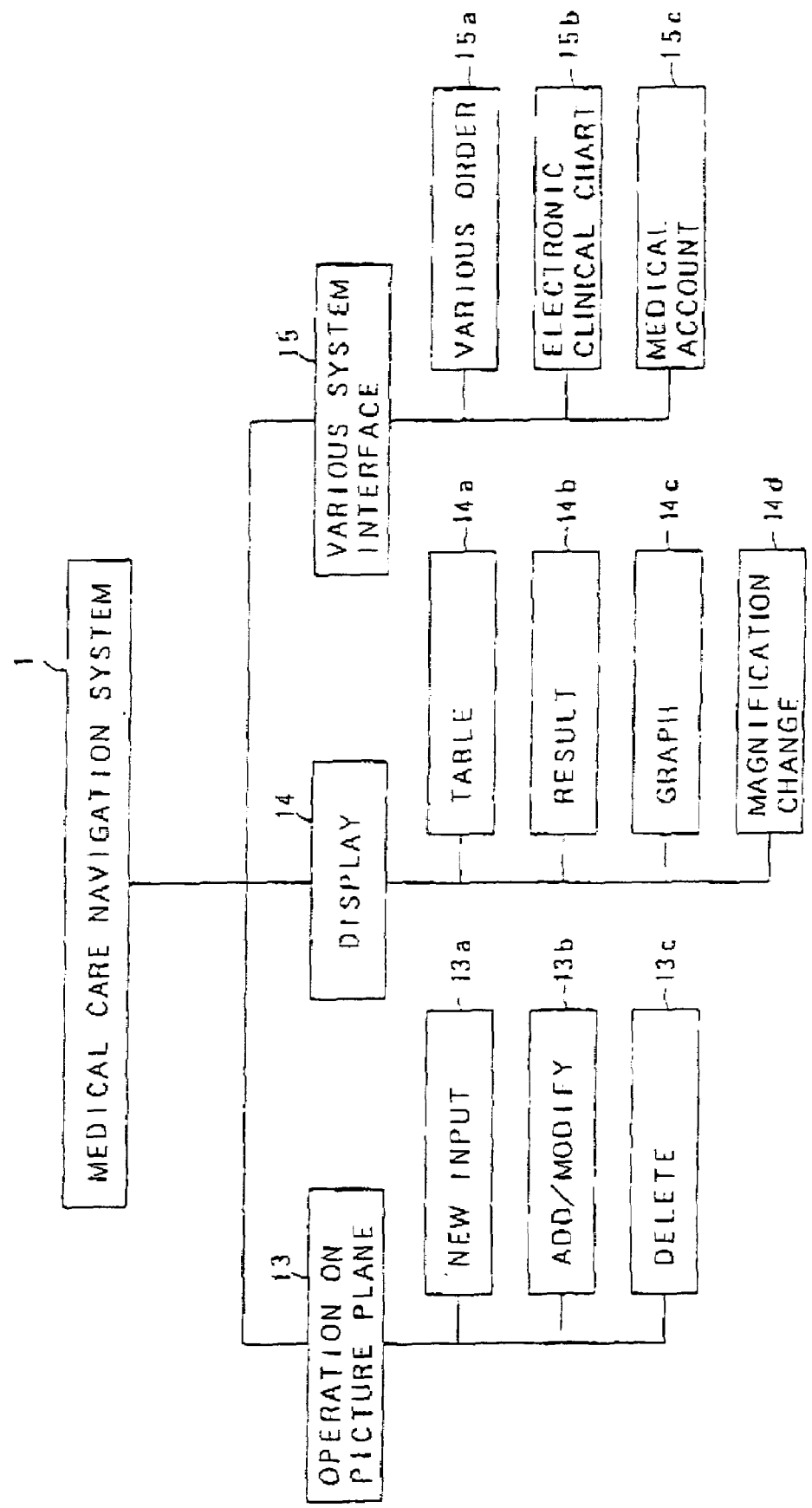
FIG. 14 is a diagram showing functions of the medical care navigation system in the embodiments.

Finally, the functions of the system for aiding to make the medical care schedule and/or record used in the above described embodiments are conceptually indicated in FIG. 14.

In FIG. 14, the function of the system 1 unifies: a function of "operation on the picture plane" 13 realized by the display device 5, the input device 3 etc. shown in FIG. 1; a function of "display" 14 realized by the display device 5 etc., a function of "various system interface" 15 realized by the communication device 7, the control device 4 etc. The function of "operation on the picture plane" 13 unifies a function of "new input" 13a, a function of "add/modify input" 13b and a function of "delete" 13c. The function of "display" 14 unifies a function of "displaying the table" 14a by use of the medical care data in the predetermined format (refer to FIG. 2 and FIG. 3 ), a function of "displaying the result" 14b by use of the medical care data and/or the detail medical data, a function of "displaying the graph" 14c for displaying the graph by use of the detail medical data, and a function of "magnification change" 14d for changing the magnification of picture plane of the display device 5.

Further, the function of "various system interfaces" 15 unifies a function of "various order" 15a for sending an order between each medical care navigation units, a function of "electronic clinical chart" 15b used by the operation unit in medical examination, and a function of "medical account" 15c used in the operation unit for account. The various order function 15a is used in a terminal unit for medicine, which is constructed to graphically-output a medicine list after receiving a medicine order through a communication device from each system interface e.g., from a clinical division. In the present embodiments, on the basis of the order information included in each of the first object files 21, it is possible to speedily issue the order corresponding to each medical care action.

The electronic clinical chart function 15b is used in a terminal unit for clinic, which is constructed to graphically output the clinic chart by use of various data received through the communication device from each system interface. The medical account function 15c is used in a terminal unit for accounting which is constructed to perform a calculation for the medical account by use of various data received through the communication device from each system interface and to graphically output the medical account book on the basis of the result of calculation.

In this manner, since the functions are unified in the multiple layered structure, each function can be efficiently called and mutual functions organically combined to each other can be performed by the system 1, which is convenient.

As described above in detail, according to each of the present embodiments, even if there is enormous medical care information, the medical information to which one would like to refer according to an individual condition can be easily referred and long term's information can be treated in a united manner.

The invention may be embodied in other specific forms without departing from the spirit or essential characteristics thereof The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

Especially, the above explained present invention can be applied to not only a medical care in a hospital but also medical care attendance or nursing, a medical care in house or home, preventive medical care, a health care, a health management, a health promotion schedule, and so on.

The entire disclosure of Japanese Patent Application No. 2000-314394 filed on Oct. 13, 2000 including the specification, claims, drawings and summary is incorporated herein by reference in its entirety.

What is claimed is:

1. A system for aiding to make a medical care schedule and/or record comprising:

a plurality of files each for including medical care data indicating one of a plurality of types of medical care actions, which are set in advance, in correlation with execution timing data indicating an execution timing of each one of the medical care actions;

a display controlling device for (i) generating first display data to display the medical care data composing the medical care schedule and/or record for one patient in a format of a medical care schedule and record table, (ii) arranging the medical care data in first rows for each type of the medical care actions and in second rows orthogonal to said first rows for each date, as for only part of the types of medical care actions for said one patient and as for only a partial period of a whole period of the medical care schedule and/or record for said one patient, on the basis of the medical care data and the execution timing data included in said files, and (iii) generating second display data to display a table identification mark information individually for each part of the types of medical care actions, which is to identify the medical care schedule and record table for said one patient, as a patient chronological table exclusive for said one patient in which the table identification mark information is arranged at a position corresponding to the partial period on a time axis indicating the whole period of the medical care schedule and/or record;

a display device for displaying the medical care schedule and record table on the basis of the first display data, and displaying the patient chronological table on the basis of the second display data; and a selecting device for selecting one of a plurality of table identification mark information under a condition that the patient chronological table comprising the plurality of table identification mark information is displayed by said display device, said plurality of files being correlated with one or a plurality of medical care schedule and record tables, each of which are identified by said plurality of table identification mark information and each of which can be displayed by said display device, said display controlling device taking out the file or files correlated with the medical care schedule and record table identified by the table identification mark information selected by said selecting device, to thereby generate the first display data by using the medical care data stored in the taken out file or files, one of said plurality of medical care schedule and record tables, which corresponds to the table identification mark information, being selected by said selecting device, the selected one of the medical care schedule and record tables being displayed by said display device on the basis of the generated first display data.

2. A system according to claim 1, wherein said plurality of files each include (i) corresponding type data indicating to which type of the medical care actions the medical care data stored in each file is to belong and (ii) priority order data indicating a priority order of the types of the medical care actions indicated by the corresponding type data, and said display controlling device generates the first display data to display the medical care schedule and record table by referencing the medical care data stored in the taken out file or files and determining to which type of the medical care actions the referenced medical care data is to belong in the selected one of the medical care schedule and record tables, on the basis of the corresponding type data and the priority order data included in the taken out file or files.

3. The system according to claim 2, wherein said display controlling device generates the first display data such that the medical care data stored in the same taken out file or files belongs to mutually different types of medical care actions, in accordance with which one of said plurality of medical care schedule and record tables is selected by said selecting device, on the basis of the corresponding type data and the priority order data, and the medical care data stored in the plurality of files is used commonly between the plurality of medical care schedule and record tables.

4. A system according to claim 1, further comprising a magnified portion specifying device for specifying one portion of the patient chronological table as a portion to be magnified under a condition that the patient chronological table is displayed by said display device, said display controlling device generates the second display data to magnify and display the one portion of the patient chronological table specified by said magnified display portion specifying device.

5. A system according to claim 1, wherein said display controlling device generates the second display data to display text information given to each of the table identification mark information at a position adjacent to each of the table identification mark information in the patient chronological table.

6. A system according to claim 1, further comprising a pop-up specifying device for specifying one of the displayed plurality of table identification mark information as one to be pop-up-displayed, under a condition that the patient chronological table including the plurality of table identification mark information is displayed by said display device, said display controlling device generating the second display data to pop-up-display detail information given to the table identification mark information specified by said pop-up specifying device at a position adjacent to the table identification mark information specified by said pop-up specifying device in the patient chronological table.

7. A system according to claim 1, wherein said display controlling device generates the second display data to display the table identification mark information in a bar shape, which has a length corresponding to a period covered by the medical care schedule and record table identified by the pertinent table identification mark information with respect to the time axis.

8. A system according to claim 1, wherein said display controlling device generates the second display data to display the table identification mark information in a point shape indicating the date of an execution of one medical care data, which is related to a predetermined type, on the time axis among the plurality of medical care data constituting the medical care schedule and record table identified by the table identification mark information.

9. A system according to claim 8, wherein said display controlling device generates third display data to display a list of the respective table identification mark information in the point shape and text information given to the respective table identification mark information, said display device displaying the list on the basis of the third display data.

10. A system according to claim 1, wherein said display controlling device generates the second display data so as to add an age of said one patient as well as at least year and month of chronological era as a scale with respect to the time axis.

11. A system according to claim 1, wherein said display controlling device generates the second display data to further display a clinical data existence period mark information in the patient chronological table, said clinical data existence period mark information indicating a clinical data existence period, in which clinical data related to one series of clinical actions among the medical care data exist and being shaped in a bar having a length corresponding to the clinical data existence period on the time axis.

12. A system according to claim 1, further comprising a date and time measuring device for measuring a present date and time, wherein said display controlling device generates the second display data to further display a present date and time mark indicating the measured present date and time within the patient chronological table.

13. A system according to claim 1, further comprising a date and time measuring device for measuring a present date and time, wherein said display controlling device generates the first display data to further display a present date and time mark indicating the measured present date and time within the medical care schedule and record table.

14. A system according to claim 1, further comprising an input device for inputting the medical care data on the medical care schedule and record table.

15. A system according to claim 1, wherein each of said files comprises an object file for including the medical care data and the execution timing data and further including procedure information, in accordance with which said display controlling device generates the first display data.

16. A system according to claim 1, wherein said system comprises two units communicated to each other through a communication line, wherein
said files are provided in one of the two units, and
said display device is provided in another of the two units.

17. A program storage device readable by a system for aiding to make a medical care schedule and/or record, tangibly embodying a program of instructions executable by said system to perform method processes for aiding to make a medical care schedule and/or record, said system comprising a plurality of files each for including medical care data indicating one of a plurality of types of medical care actions, which are set in advance, in correlation with execution timing data indicating an execution timing of each one of the medical care actions, said method processes comprising the processes of:

generating second display data to display a table identification mark information individually for each part of the types of medical care actions to identify a medical care schedule and record table for said one patient and arranging the medical care data in first rows for each type of the medical care actions and in second rows orthogonal to said first rows for each date, as a patient chronological table exclusive for said one patient in which the table identification mark information is arranged at a position corresponding to only a partial period of a whole period of the medical care schedule and/or record for one patient on a time axis indicating the whole period of the medical care schedule and/or record;

displaying the patient chronological table on the basis of the second display data;

selecting one of a plurality of table identification mark information under a condition that the patient chronological table comprising the plurality of table identification mark information is displayed, said plurality of files being correlated with one or a plurality of medical care schedule and record tables, each of which are identified by said plurality of table identification mark information and each of which can be displayed by said display device;

taking out the file or files correlated with the medical care schedule and record table identified by the table identification mark information selected by said selecting process;

generating first display data to display the medical care data composing the medical care schedule and record in a format of the medical care schedule and record table as for only part of the types of medical care actions for said one patient and as for only the partial period of the medical care schedule and record for said one patient, on the basis of the medical care data and the execution timing data included in said taken out file or files; and displaying the medical care schedule and record table on the basis of the first display data, one of said plurality of medical care schedule and record tables, which corresponds to the table identification mark information, being selected by said selecting process, the selected one of the medical care schedule and record tables being displayed by said display process on the basis of the generated first display data.

18. A method for aiding to make a medical care schedule and/or record in a system for aiding to make the medical care schedule and/or record, said system comprising a plurality of files each for including medical care data indicating one of a plurality of types of medical care actions, which are set in advance, in correlation with execution timing data indicating an execution timing of each one of the medical care actions, said method comprising the processes of:

generating second display data to display a table identification mark information individually for each part of the types of medical care actions to identify a medical care schedule and record table for said one patient and arranging the medical care data in first rows for each type of the medical care actions and in second rows orthogonal to said first rows for each date, as a patient chronological table exclusive for said one patient in which the table identification mark information is arranged at a position corresponding to only a partial period of a whole period of the medical care schedule and/or record for one patient on a time axis indicating the whole period of the medical care schedule and/or record;

displaying the patient chronological table on the basis of the second display data;

selecting one of a plurality of table identification mark information under a condition that the patient chronological table comprising the plurality of table identification mark information is displayed, said plurality of files being correlated with one or a plurality of medical care schedule and record tables, each of which are identified by said plurality of table identification mark information and each of which can be displayed by said display device;

taking out the file or files correlated with the medical care schedule and record table identified by the table identification mark information selected by said selecting process;

generating first display data to display the medical care data composing the medical care schedule and record in a format of the medical care schedule and record table as for only part of the types of medical care actions for said one patient and as for only the partial period of the medical care schedule and record for said one patient, on the basis of the medical care data and the execution timing data included in said taken out file or files; and displaying the medical care schedule and record table on the basis of the first display data, one of said plurality of medical care schedule and record tables, which corresponds to the table identification mark information, being selected by said selecting process, the selected one of the medical care schedule and record tables being displayed by said display process on the basis of the generated first display data.

* * * * *